US012778488B2

(12) United States Patent
Lee et al.

(10) Patent No.: US 12,778,488 B2
(45) Date of Patent: Nov. 3, 2026

(54) SYSTEMS, METHODS, AND APPARATUSES FOR NEUROLOGICAL ACTIVITY DATA ANALYSIS

(71) Applicant: LVIS Corporation, Palo Alto, CA (US)

(72) Inventors: Jin Hyung Lee, Palo Alto, CA (US); Zhongnan Fang, Santa Clara, CA (US)

(73) Assignee: LVIS Corporation, Palo Alto, CA (US)

( * ) Notice: Subject to any disclaimer, the term of this patent is extended or adjusted under 35 U.S.C. 154(b) by 415 days.

(21) Appl. No.: 18/548,549

(22) PCT Filed: Mar. 2, 2022

(86) PCT No.: PCT/US2022/018559
§ 371 (c)(1),
(2) Date: Aug. 31, 2023

(87) PCT Pub. No.: WO2022/187388
PCT Pub. Date: Sep. 9, 2022

(65) Prior Publication Data

US 2024/0138746 A1 May 2, 2024

Related U.S. Application Data

(60) Provisional application No. 63/156,040, filed on Mar. 3, 2021.

(51) Int. Cl.
*A61B 5/00* (2006.01)
*A61B 5/369* (2021.01)
*A61B 5/384* (2021.01)

(52) U.S. Cl.
CPC ............ *A61B 5/384* (2021.01); *A61B 5/7475* (2013.01)

(58) Field of Classification Search
None
See application file for complete search history.

(56) References Cited

U.S. PATENT DOCUMENTS 9,832,587 B1 11/2017 Park et al.
2009/0312663 A1 12/2009 John et al.
2009/0318794 A1 12/2009 Decharms
(Continued)

FOREIGN PATENT DOCUMENTS

CN 111246796 A 6/2020
CN 111801046 A 10/2020
(Continued)

OTHER PUBLICATIONS

Staljanssens et al. Seizure Onset Zone Localization from Ictal High-Density EEG in Refractory Focal Epilepsy. Brain Topography (2017) 30: 257-271. (Year: 2017).*
(Continued)

*Primary Examiner* — Etsub D Berhanu
(74) *Attorney, Agent, or Firm* — Dorsey & Whitney LLP

(57) ABSTRACT

Electroencephalography (EEG) data may be analyzed to calculate various metrics such as maximum amplitude projection, node visit frequency, node transition frequency, and/or node transition polarity. The calculated metrics may be provided graphically in some examples. In some examples, the metrics may be provided graphically in combination with other data such as raw EEG traces.

15 Claims, 19 Drawing Sheets

(56) References Cited

U.S. PATENT DOCUMENTS

| | | | | |
|---|---|---|---|---|
| 2010/0049482 | A1* | 2/2010 | He | A61B 5/374 703/2 |
| 2012/0209346 | A1 | 8/2012 | Bikson et al. | |
| 2012/0296569 | A1* | 11/2012 | Shahaf | A61B 5/383 702/19 |
| 2013/0096408 | A1* | 4/2013 | He | A61B 5/4094 600/378 |
| 2015/0227702 | A1* | 8/2015 | Krishna | A61B 5/374 705/2 |
| 2018/0055394 | A1* | 3/2018 | Sohrabpour | A61B 5/367 |
| 2019/0117085 | A1* | 4/2019 | Brown | A61B 5/0205 |
| 2020/0008725 | A1 | 1/2020 | Bach et al. | |
| 2020/0114103 | A1* | 4/2020 | Richard | A61B 5/0836 |
| 2021/0369181 | A1* | 12/2021 | Nierenberg | A61B 5/055 |

FOREIGN PATENT DOCUMENTS

| | | | |
|---|---|---|---|
| EP | 1005677 | B9 | 12/2007 |
| JP | 2007289469 | A | 11/2007 |
| WO | 2007124040 | A2 | 11/2007 |
| WO | 2013007846 | A1 | 1/2013 |
| WO | 2020048593 | A1 | 3/2020 |
| WO | 2022187388 | A1 | 9/2022 |

OTHER PUBLICATIONS

Ding et al. Spatio-temporal EEG Source Localization Using a Three-dimensional Subspace FINE Approach in a Realistic Geometry Inhomogenous Head Model. IEEE Transactions on Biomedical Engineering. Sep. 2006; 53(9): 1732-1739. (Year: 2006).*

"Extended European Search Report for EP22763995.2, mailed on Dec. 11, 2024".

Liu, Ye , et al., "A Boosting-Based Spatial-Spectral Model for Stroke Patients' EEG Analysis in Rehabilitation Training", EEG Analysis in Rehabilitation Training. IEEE Trans Neural Syst Rehabil Eng. Jan. 2016;24(1):169-79. doi: 10.1109/TNSRE.2015.2466079. Epub Aug. 20, 2015. PMID: 26302519.

The International Search Report and The Written Opinion mailed on Jul. 20, 2022 for International Patent Application No. PCT/US22/18559, pp. all.

Heidrich, Wolfgang, et al., "Interactive maximum projection vol. rendering", Proceedings Visualization '95; URL: https://www.researchgate.net/profile/Michae1-Mccool/publication/3618088_1nteractive_maximum_projection_volume_rendering/links/0deec52eb65af7a641000000/Interactive-maximum-projection-volume-rendering.pdf>, 1995, pp. 11-18.

Michel, Christoph M., et al., "EEG source localization", Handbook of clinical neurology, vol. 160; URL:https://cibm.ch/wpcontent/uploads/1-s2.0-B9780444640321000060-main.pdf, 2019, pp. 85-101.

Mroz, Lukas , "Interactive High-Quality Maximum Intensity Projection", In Computer Graphics; Forum (vol. 19); URL:https://www.academia.edu/download/30969710/10.1.1.43.6956.pdf, 2000, pp. 341-350.

Rosvall, M , et al., "The map equation", The European Physical Journal Special Topics, 23; URL: https://arxiv.orQ/pdf/0906.1405, Sep. 2009, pp. 13-23.

Staljanssens , et al., "Seizure onset zone localization from ictal high-density EEG in refractory focal epilepsy", Brain topography, 30(2); URL:https://biblio.ugent.be/publication/8601524/file/8601526, 2017, pp. 257-271.

Swales, Dustin , et al., "Examining moisture pathways and extreme precipitation in the U.S. Intermountain West using self-organizing maps", Geophysical Research Letters, 19; URL:https://repository.library.noaa.gov/view/noaa/14619/noaa_ 14619 _DS 1.pdf, Feb. 2016, pp. 1727-1735.

"Office Action and Translation for JP Appl. No. 2023-553428, mailed on Nov. 13, 2025".

"Office Action and Translation for CN Appl. No. 202280018457.8, mailed on Apr. 1, 2026".

Second Office Action and Translation for CN Appl. No. 202280018457.8, mailed on Sep. 1, 2026, pp. all.

First Examination Report for Indian Application No. 202317061623, mailed on Aug. 11, 2026, pp. all.

* cited by examiner

EEG
(19 channel 10-20 Montage)

EEG Scalp at the Time of Red Line

Source Localized EEG
at the Time of the Red Line

SYSTEMS, METHODS, AND APPARATUSES FOR NEUROLOGICAL ACTIVITY DATA ANALYSIS

CROSS-REFERENCE TO RELATED APPLICATION(S)

This application is a U.S. National Stage filing under 35 U.S.C. § 371 of PCT Application No. PCT/US2022/018559, filed Mar. 2, 2022, which claims the benefit under 35 U.S.C. § 119 of the earlier filing date of earlier filed U.S. Provisional Application No. 63/156,040, filed on Mar. 3, 2021, the entire contents of which are hereby incorporated by reference in their entirety, for any purposes.

TECHNICAL FIELD

Examples described herein relate generally to processing, analyzing, and providing neurological activity data.

BACKGROUND

Data related to neurological activity may be collected from subjects by a variety of methods. For example, electroencephalography (EEG) data may be acquired by applying multiple probes (e.g., electrodes) on a subject's scalp. In some applications, the number of electrodes (e.g., channels), may be nineteen. However, other numbers of probes may be used in other applications. Electrical signals in the brain of the subject may be measured by the probes. The electrical signals may be indicative of neurological activity. In some applications, the electrical signals may be measured over time.

The EEG data may be plotted two-dimensionally (2D). For example, the electrical signals measured by each probe may be plotted over time. Each plot may be referred to as a trace. An example of 2D EEG traces are shown in FIG. 1, image a. Reading 2D EEG traces (e.g., plots of the magnitude of the electrical signals over time) to recognize seizures and determine characteristics of the seizures, such as inferring the underlying neural activity of the seizure requires years of training. Even experts typically cannot tell the precise location of the neural activity (e.g., a seizure) from EEG data alone. This limits the diagnostic and research value of EEG traces.

SUMMARY

According to examples disclosed herein, electroencephalography data may be analyzed to calculate various metrics (also referred to as parameters) such as maximum amplitude projection, node visit frequency, node transition frequency, and/or node transition polarity. These metrics may be displayed, stored, and/or utilized to diagnose patient(s), determine or adjust treatment plans, and/or take other actions.

According to examples of the present disclosure, a system may include at least one processor and a memory accessible to the at least one processor, the memory encoded with computer-readable instructions that when executed, cause the system to calculate at least one metric comprising a maximum amplitude projection, a node visit frequency, a node transition frequency, a node transition polarity, or a combination thereof, from neurological activity data. In some examples, the neurological activity data comprises electroencephalography data.

In some examples, the system may further include a display communicatively coupled to the at least one processor, wherein the computer-readable instructions when executed, further cause the system to provide a graphical representation of the at least one metric on the display. In some examples, graphical representation of the at least one metric comprises a node of a three dimensional source localization overlaid on an image of a brain.

In some examples, the system may further include a display communicatively coupled to the at least one processor, wherein the computer-readable instructions when executed, further cause the system to provide a report on the display, wherein the report comprises a plurality of contents comprising one or more graphical representations of the at least one metric and further comprises a timeline of the neurological activity data, one or more statistics, one or more additional parameters, or a combination thereof. In some examples, the system may further include an input device configured to receive a user input, wherein the user input indicates which ones of the plurality of contents are included in the report.

In some examples, a method may include receiving neurological activity data and calculating at least one metric comprising a maximum amplitude projection, a node visit frequency, a node transition frequency, a node transition polarity, or a combination thereof, from the neurological activity data. In some examples, the neurological activity data comprises a three dimensional (3D) source localization comprising a plurality of nodes, wherein individual ones of the plurality of nodes corresponds to a portion of a brain.

In some examples, calculating the maximum amplitude projection of a node of the plurality of nodes may include finding a number of times the node of the plurality of nodes is labeled as a local maximum within an analysis time window and determining a maximum value of the local maximum from the number of times the node of the plurality of nodes is labeled as the local maximum.

In some examples, calculating the node visit frequency for a node of the plurality of nodes includes counting a number of times the node of the plurality of nodes is labeled as a local maximum within an analysis time window and dividing the number of times by a duration of the analysis time window.

In some examples, calculating the node transition frequency includes counting a number of transitions between a first local maximum node and a second local maximum node of the plurality of nodes within an analysis time window and dividing the number of times by a duration of the analysis time window.

In some examples, calculating the node transition polarity for a node of the plurality of nodes includes counting a first number of times a local maximum transitioned to the node of the plurality of nodes from one or more nodes of the plurality of nodes, counting a second number of times the local maximum transitioned from the node of the plurality of nodes to one or more nodes of the plurality of nodes, and taking a difference of the first number of times and the second number of times. In some examples, the node of the plurality of nodes has an inward polarity when the first number of times is greater than the second number of times and the node of the plurality of nodes has an outward polarity when the second number of times is greater than the first number of times.

In some examples, the method may further include preprocessing the neurological data by comparing values of the neurological activity data to a threshold value, based on the comparing, discarding or ignoring one or more of the values of the neurological activity data, and from remaining values of the neurological activity data, calculating at least one local maximum.

In some examples, the method may further include providing a graphical representation of the at least one metric on a display. In some examples, the graphical representation of the at least one metric comprises a node of a three dimensional (3D) source localization overlaid on an image of a brain. In some examples, a size of the node is proportional to a value of the maximum amplitude projection or a value of the node visit frequency for the node. In some examples, a shade, a color, or a combination thereof of the node, is indicative of a value for the maximum amplitude projection, the node visit frequency, or the node transition polarity for the node. In some examples, the graphical representation further comprises a second node of the 3D source localization and an arrow between the node and the second node, wherein a direction of the arrow indicates a transition of a local maximum between the node and the second node. In some examples, a shade, a color, or a combination thereof of the arrow indicates a frequency of the transition over an analysis time window.

In some examples, the method may further include providing a report on a display, wherein the report comprises a plurality of contents comprising one or more graphical representations of the at least one metric and further comprises a timeline of the neurological activity data, one or more statistics, one or more additional parameters, or a combination thereof.

DETAILED DESCRIPTION

Certain details are set forth below to provide a sufficient understanding of described embodiments. However, it will be clear to one skilled in the art that embodiments may be practiced without these particular details. In some instances, well-known EEG techniques and systems, circuits, control signals, timing protocols, and/or software operations have not been shown in detail in order to avoid unnecessarily obscuring the described embodiments.

As noted, electroencephalography (EEG) data may be acquired by applying multiple probes (e.g., electrodes) on a subject's scalp. In some applications, the locations of the probes with respect to the brain of the subject and/or with respect to the other probes may be known. The electrical signals recorded by the probes as EEG data may be indicative of neurological activity (e.g., electrical or electrochemical activity in the brain). The collected EEG data may then be visualized by various techniques.

Figure 1A:
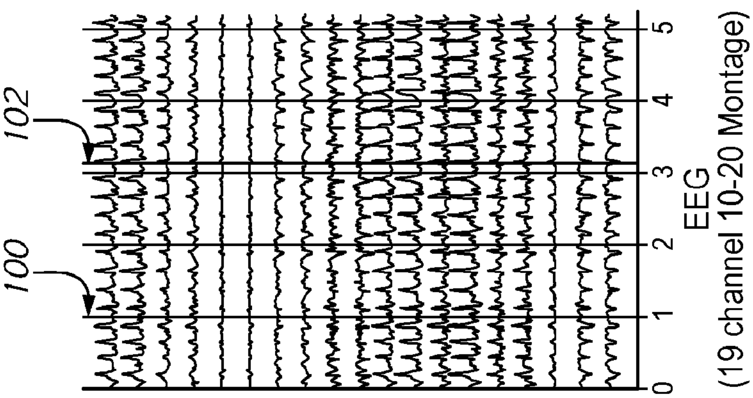
FIG. 1A-C illustrate examples of visualizing EEG data according to examples of the present disclosure.
Figure 1B:
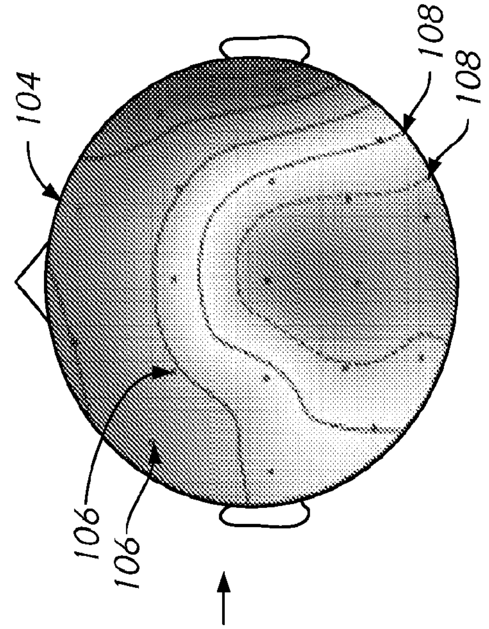
Figure 1C:
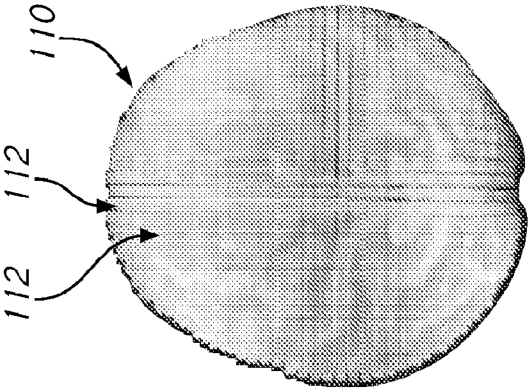

FIG. 1 illustrates examples of visualizing EEG data according to examples of the present disclosure. Initially, EEG data is acquired from multiple probes as described above. The EEG data includes electrical signals acquired over time by each probe. An example of a 2D plot 100 of the electrical signals detected and recorded by each probe is shown at image a of FIG. 1. However, as noted previously, reading of the EEG traces of plot 100 to understand the underlying neurological activity is difficult and time consuming.

The electrical signals recorded by each probe may be used to generate a contour map of the scalp indicating the intensity of the electrical signals in various regions. An example contour map 104 is shown in image b of FIG. 1. The contour map 104 was generated from the EEG data in plot 100 at a time point indicated by vertical line 102. The dots 106 indicate locations of the probes on the scalp of the subject. Contour lines 108 indicate the slope of changes in intensity of the electrical signal, similar to contours on a topographical map indicating slope of changes in elevation. In some contour maps, such as contour map 104, shading in different tones and/or colors may be used to indicate intensity and/or polarity of the recorded electrical signals. While the contour map 104 provides an intuitive view of the data in plot 100, the data is extrapolated to a surface of the subject's head, and only a general understanding of the portions of the brain involved in the electrical activity may be achieved.

Based, at least in part, on the electrical signals (such as those shown in plot 100) and the locations, electrical signals may be localized to one or more locations in the brain (e.g., the location of the origin of a brain signal may be determined and/or estimated). These locations may be referred to as source localization nodes or simply nodes. For example, a node may refer to a portion of a brain. Any size portion may be used to constitute a node. These nodes may form a three dimensional (3D) grid corresponding to locations within a subject's brain. In some examples, the 3D grid may be Cartesian grid where locations are described with reference to three axes (e.g., x, y, z). However, other grid/coordinate systems may be used in other examples. The size of the nodes, the number of nodes and/or distance between nodes in the 3D grid may be based on one or more factors. Example factors include, but are not limited to, sensitivity and/or specificity of the EEG probes, number of EEG probes, and signal-to-noise ratio of EEG data. Each node of the 3D grid may have one or more values associated with the electrical signals attributed to that node (e.g., magnitude, polarity) to form a 3D (volume) EEG data set.

The 3D data set may be rendered as an image for visualization. The 3D data set and/or resulting image may be referred to as a 3D source localization. In some examples, the 3D source localization may be rendered as an overlay on an image of a brain. This may provide a visual guide as to which nodes correspond to which regions of the brain. The brain may be rendered translucent to permit visualization of the 3D source localization in some examples. In some examples, the image of the brain may be rendered from a model or from an image acquired from the subject (e.g., computed tomography, MRI). An example of a source localization 110 is shown in image c of FIG. 1. The source localization 110 was generated from the EEG data in plot 100 at a time point indicated by vertical line 102. The nodes 112 are illustrated by individual cubes. However, in other examples, other shapes may be used to visualize the nodes 112 (e.g., spheres, irregularly shaped volumes). In some examples, different tones and/or colors may be used for the nodes 112 to indicate intensity and/or polarity of the recorded electrical signals. Although the source localization 110 shown in FIG. 1 is a top-down view, source localization 110 may be a 3D data set that is capable of being viewed from multiple angles and/or locations (e.g., views generated closer or farther from the 3D data set, views generated from within the 3D data set, views of "slices" of the volume of the 3D data set, etc.).

Figure 2:
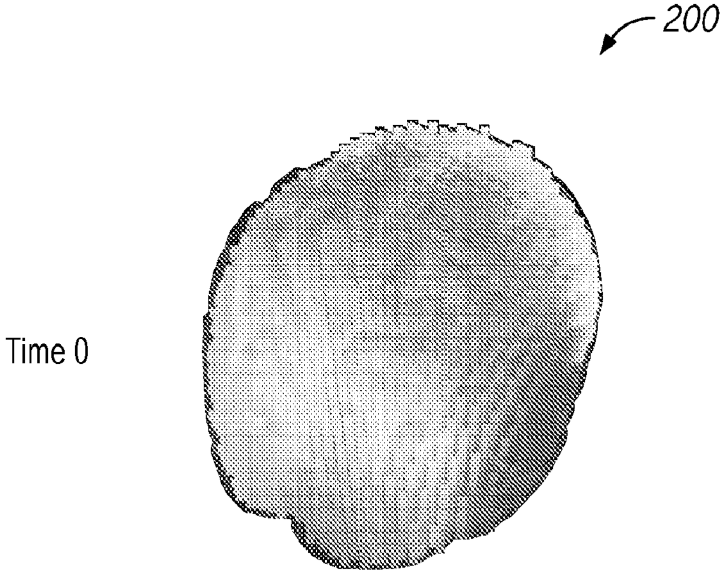
FIG. 2 illustrates two example 3D source localizations from a same subject at different points in time according to examples of the present disclosure.
Figure 2:
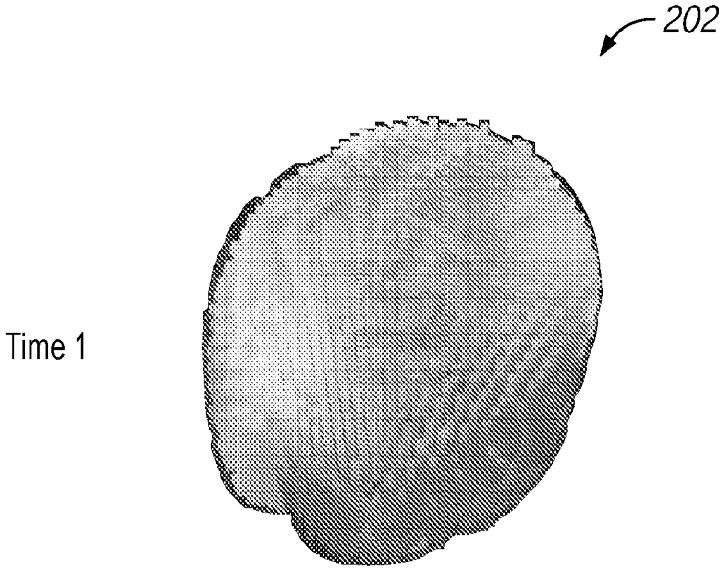

Four-dimensional (4D) EEG data refers to viewing the 3D EEG data over time. For example, a 3D image may illustrate the electrical signals at each node for a time point, and the 4D EEG data may be a series of 3D images, each representing electrical activity at a different point in time. In some examples, each time point may be a period of time (e.g., microseconds, milliseconds, seconds) over which the electrical signals for each node are summed, averaged, or otherwise combined. 4D EEG data may allow visualization of source localization (e.g., 4D source localization), such as seizure source localization, which describes where a seizure starts and travels within the brain. FIG. 2 illustrates two example 3D source localizations from a same subject at different points in time according to examples of the present disclosure. The two 3D source localizations 200, 202 at Time 0 and Time 1, respectively, may represent a 4D seizure source localization or a portion of a 4D seizure source localization. In the example shown in FIG. 2, different shading is used to indicate the electrical signals attributed to the individual nodes. The shading of several of the nodes changes from Time 0 to Time 1, indicating how the electrical activity at different locations in the brain vary over time.

The 4D seizure source localization may be more intuitive and easier to understand than 2D EEG traces. However, the proper values for the time range, angle of view, distance of views, and display thresholds are required to generate an understandable 4D visualization. In some applications, a user may need to find the proper values empirically. This may make preparing and reading 4D seizure source localization data time consuming.

According to embodiments of the present disclosure, one or more metrics may be calculated that summarize the 4D seizure source localization. In some applications, this may reduce the time necessary to generate and/or interpret 4D seizure source localization. According to examples disclosed herein, EEG data (e.g., traces of electrical signals recorded by one or more electrodes over time) acquired from a subject may be analyzed to calculate one or more metrics such as maximum amplitude projection, node visit frequency, node transition frequency, and/or node transition polarity. These metrics may then be provided in various formats, such as through text, charts, generated images, or a combination thereof. The metrics may be used to diagnose, to determine and/or adjust treatment, and/or to take other actions.

Although the examples disclosed herein refer to EEG data, this is merely for illustration, and the embodiments are not limited to EEG data. Some or all of the techniques disclosed herein may be applied to other neurological activity data that can be associated with locations within the brain such as functional magnetic resonance imaging (fMRI) data, electrocorticography data, magnetoencephalography data, near infrared spectroscopy data, and event-related optical signal data. Furthermore, although the examples disclosed herein refer to seizure localization, some or all of the techniques disclosed herein may be applied to localization of other neural activity (e.g., responses to stimulations, responses to treatment).

In some examples, the data of the 4D seizure source localization, that is, the 3D data set for each time point, may be preprocessed. Preprocessing may include calculating local maximums for individual source localizations at multiple time points in some examples, there may be multiple local maximums for individual source localizations at individual time points in some examples. In some examples, the local maximums may be based on amplitudes, magnitudes, polarities, frequencies of the electrical signals at the nodes, or a combination thereof. In some examples, a user may set a threshold value for a minimum value of the local maximums. In other words, the neurological data may be preprocessed by comparing values of the neurological data to a threshold value. Based on the comparison, some of the neurological data may be discarded or ignored. From the remaining (not discarded or ignored) data, local maximums for the neurological data may be computed.

Figure 3:
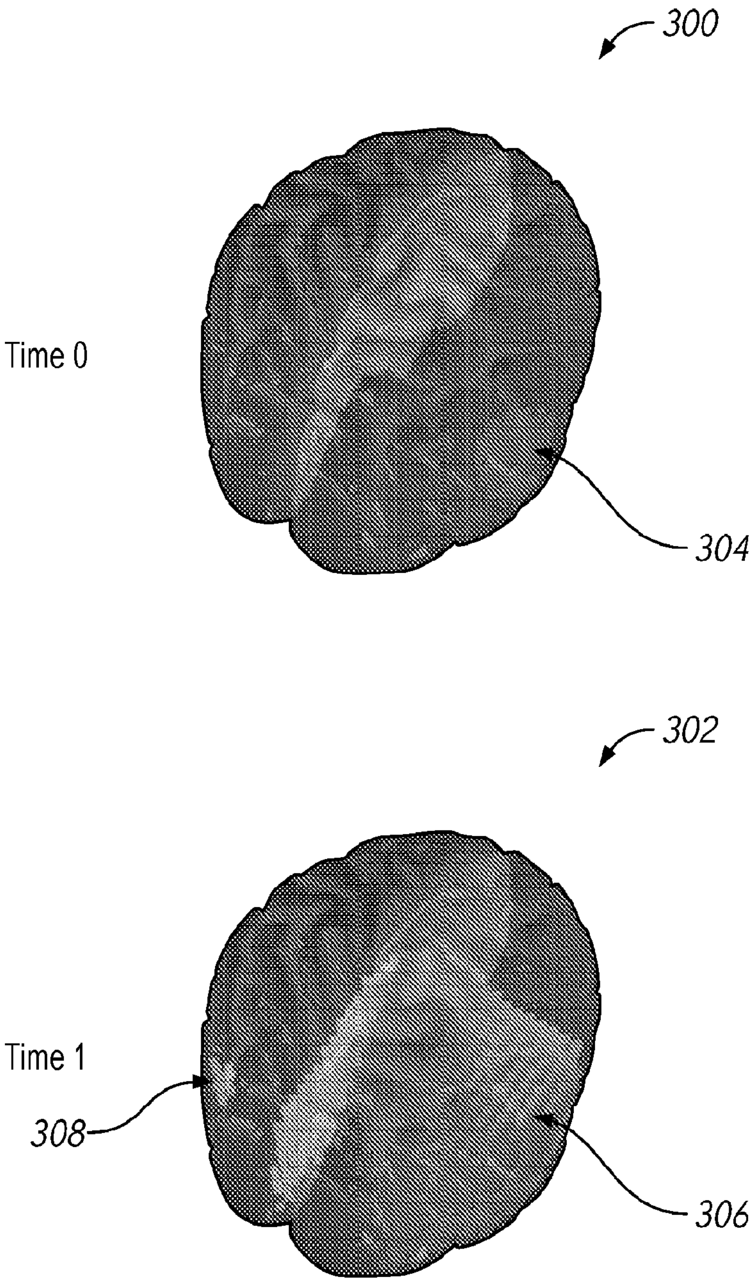
FIG. 3 illustrates an example of thresholded 3D source localizations according to examples of the present disclosure.

FIG. 3 illustrates an example of thresholded 3D source localizations according to examples of the present disclosure. The thresholded 3D source localizations 300, 302 are generated the 3D source localizations 200, 202, respectively, shown in FIG. 2 based on a minimum value of the local maximums. In the example shown in FIG. 3, the 3D source localization 300 includes a region 304 that meets or exceeds the minimum value of the local maximums and 3D source localization 202 includes regions 306 and 308 that meets or exceeds the minimum value of the local maximums as indicated by the shaded portions. In some examples, the data related to local maximums that do not meet or exceed the minimum value of the local maximums may be discarded or ignored in further computations.

Figure 4:
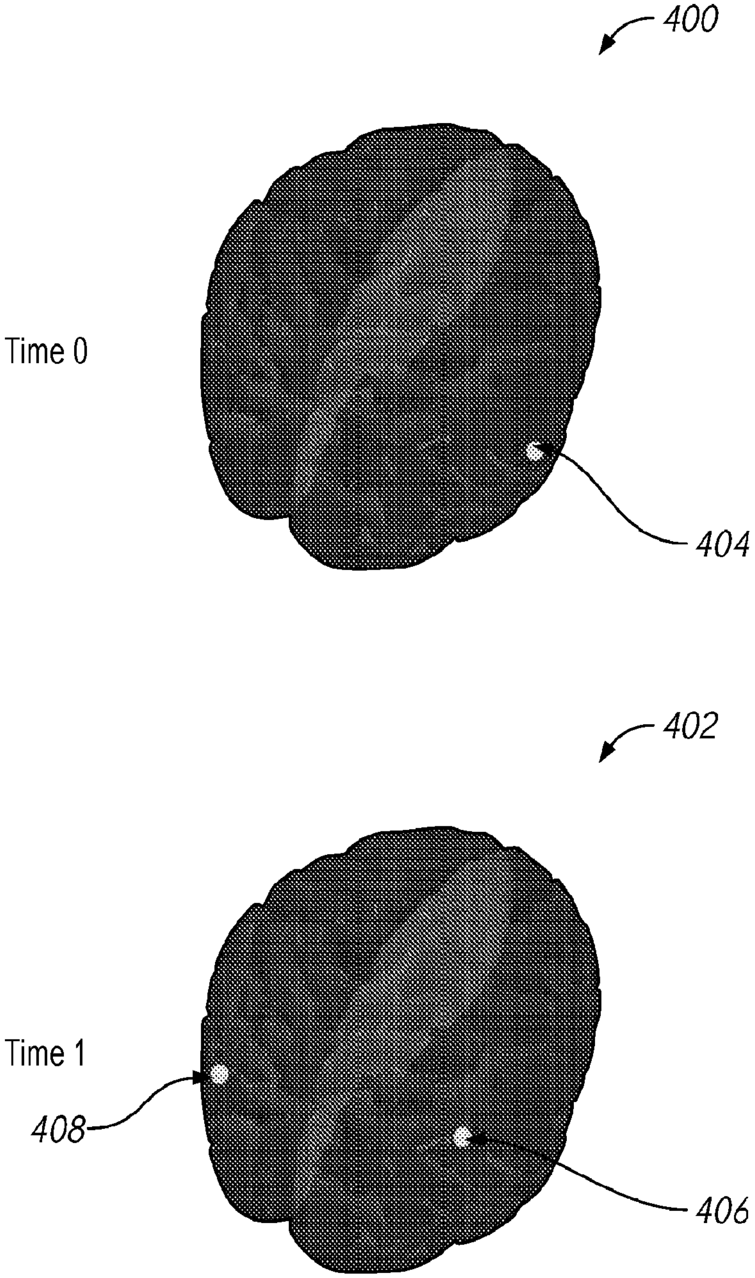
FIG. 4 illustrates an example of local maximums identified in the 3D source localizations according to examples of the present disclosure.

FIG. 4 illustrates an example of local maximums identified in the 3D source localizations according to examples of the present disclosure. The 3D source localizations 400, 402 are generated from the thresholded 3D source localizations 300, 302, respectively, shown in FIG. 3. The highlighted node 404 indicates the local maximum for the region 304 and highlighted nodes 406 and 408 indicate the local maximums for regions 306 and 308, respectively.

In some examples, after preprocessing, such as the preprocessing described with reference to FIGS. 3 and 4, various metrics may be computed. Graphical representation of the results of the computations of the metrics may be displayed as one or more images. For example, one or more nodes corresponding to the nodes of the 4D source localization may be provided as spheres, cubes, or other graphical representation in an image. The nodes may be located in the image at a location corresponding to the location of the node when displayed with the entire 3D grid of the source localization. In some examples, the nodes may be overlaid on an image of a brain. The image of the brain may be the subject's brain or a rendering of a brain model.

In some examples, maximum amplitude projection may be computed for the 4D source localization. The maximum amplitude projection may indicate regions of the brain that have high amplitude electrical signals over various time points, such as during a seizure. The maximum amplitude projection may be calculated by analyzing individual source localization nodes of the 3D source localizations across time. The time period over which the 3D source localizations are analyzed (e.g., the analysis time window) may extend over the entire time period covered by the 4D source localization (e.g., an entire time period over which the EEG trace was acquired) or a subset of the time period. Example analysis time windows include 1 ms, 5 ms, 10 ms, 20 ms, 50 ms, 100 ms, 1 sec, and 30 sec. Other analysis time windows may be used in other examples.

If a node was labeled as a local maximum point (e.g., nodes 404, 406, 408) at least once within the analysis time window, the maximum amplitude projection will output the maximum source localization amplitude of the node within the analysis window. If a node was never labeled as a local maximum within the analysis time window, no output will be provided for the node. In some embodiments, the output of the maximum amplitude projection may have a same unit as the unit used for the 3D source localization (e.g., arbitrary unit for standard low-resolution brain electromagnetic tomography (sLORETA) source localization, picoampermeter (pA-m) for minimum-norm estimate (MNE) source localization).

Figure 5:
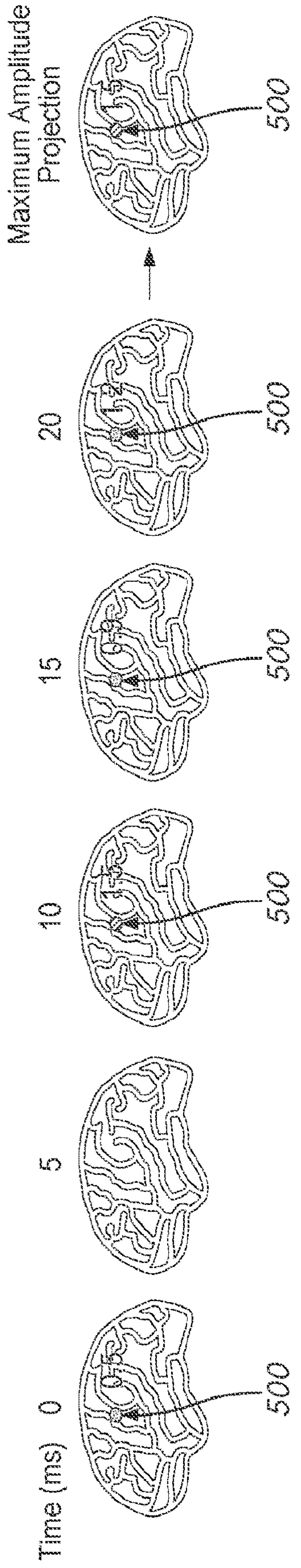
FIG. 5 graphically illustrates an example computation of a maximum amplitude projection for a node according to examples of the disclosure.

FIG. 5 graphically illustrates an example computation of a maximum amplitude projection for a node according to examples of the disclosure. A node 500 is labeled as a local maximum at times 0 ms, 10 ms, 15 ms, and 20 ms within an analysis time window. The value of node 500 when a local maximum is 0.5, 1.5, 0.9, and 1.2, respectively. The maximum value of node 500 within the analysis time window is 1.5, which occurs at time 10 ms. Accordingly, the output of the maximum amplitude projection for node 500 is 1.5. Although the example computation in FIG. 5 is for one node, it is understood that the procedure shown is performed for all nodes, or all nodes labeled as a local maximum at least once within the analysis time window.

Figure 6:
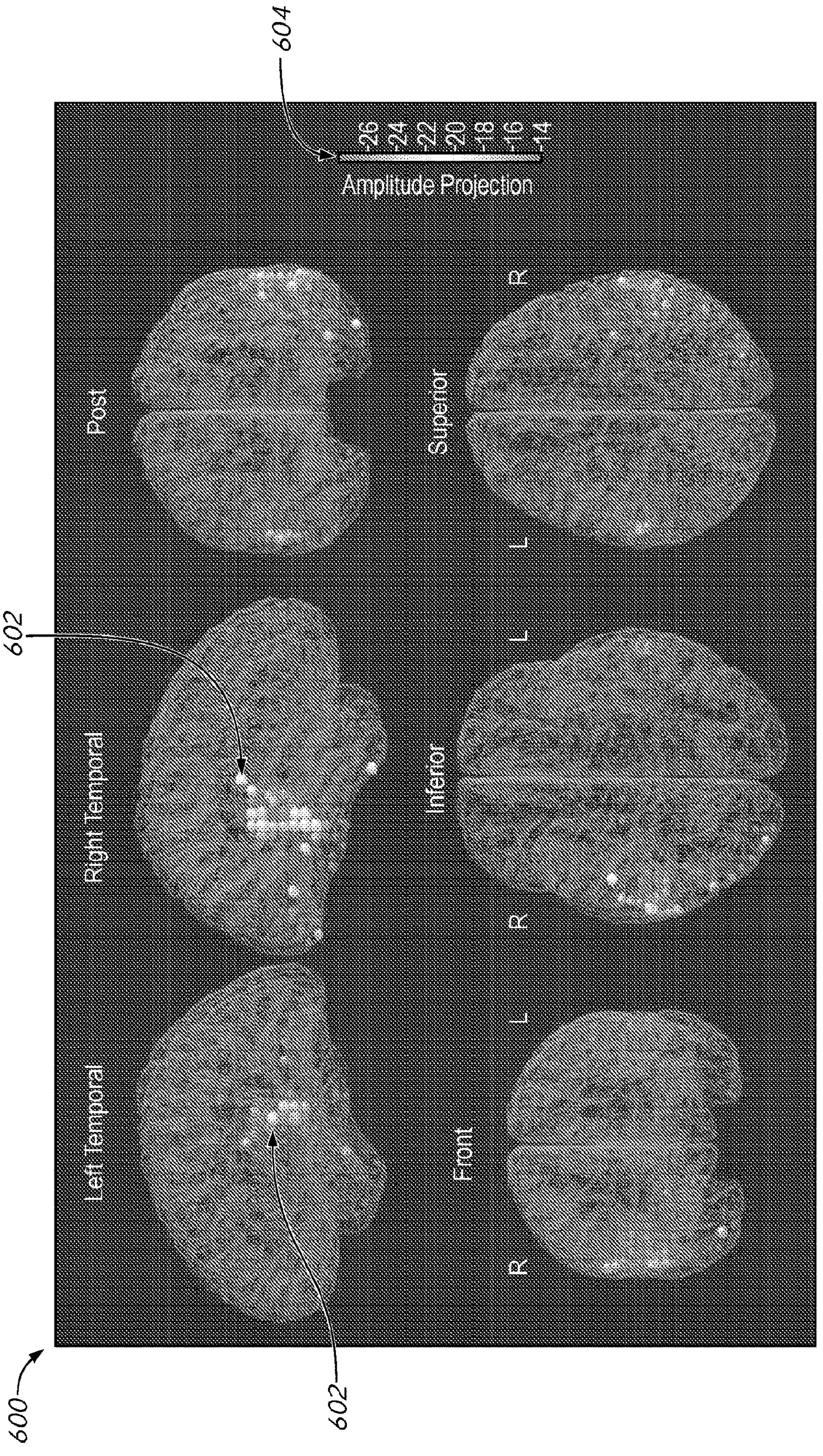
FIG. 6 is an example of a maximum amplitude projection result of a seizure according to examples of the disclosure.

FIG. 6 is an example of a maximum amplitude projection result of a seizure according to examples of the disclosure. The result 600 is shown in left, right, posterior, anterior, inferior and superior view of the same brain (L: Left, R: Right side of the brain). In the example shown in FIG. 6, the size of a node 602 is quadratically proportional to its value (e.g., maximum amplitude) and a shade of the node 602 corresponds to its value as indicated by the legend 604. However, other visualization techniques for conveying the value of the maximum amplitude projection may be used in other examples (e.g., colors, shapes, text indicating the numerical value).

Although maximum amplitude is described, other amplitude projections (e.g., based on user-selected thresholds), may be computed in a similar manner. The maximum amplitude projection may provide information regarding severity and/or most reactive regions of the brain during certain neural events (e.g., seizure).

In some examples, node visit frequency may be computed for the 4D source localization. The node visit frequency may indicate brain regions that are frequently active during a time period. The node visit frequency may provide insights into which regions of the brain are most frequently active during a neurological event. The node visit frequency may be calculated for source localization nodes, such as source localization nodes associated with local maximums, across a given analysis time window. For individual source localization nodes, the number of times that the node is labeled as a local maximum may be counted. In some examples, the output may be the number of counts (e.g., visits). In some examples, the number may then be divided by a duration of the analysis time window. In these examples, the output may have a unit of counts per unit of time (e.g., ms, sec).

Figure 7:
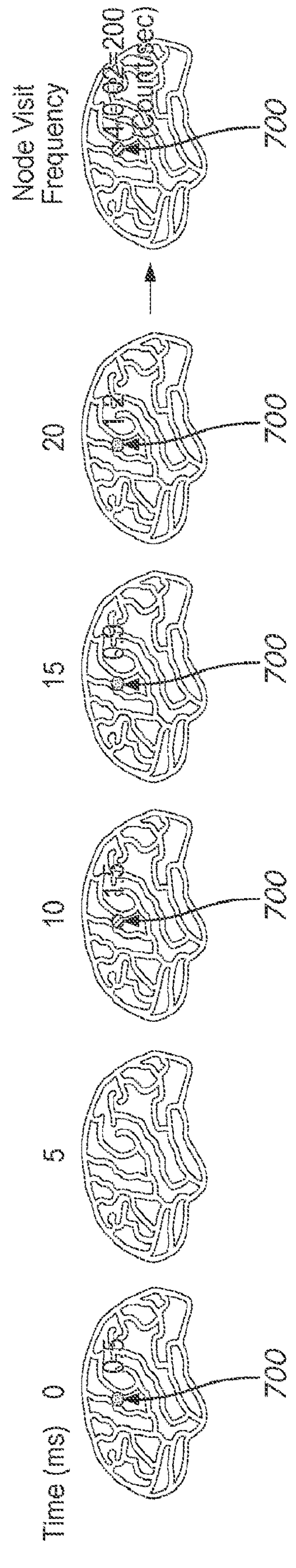
FIG. 7 graphically illustrates an example computation of a node visit frequency for a node according to examples of the disclosure.

FIG. 7 graphically illustrates an example computation of a node visit frequency for a node according to examples of the disclosure. A node 700 is labeled as a local maximum four times at times 0 ms, 10 ms, 15 ms, and 20 ms within an analysis time window having a duration of 20 ms. The number of times (4) is divided by the duration of the analysis time window (0.02 sec) for a node visit frequency of 200 counts/sec.

Figure 8:
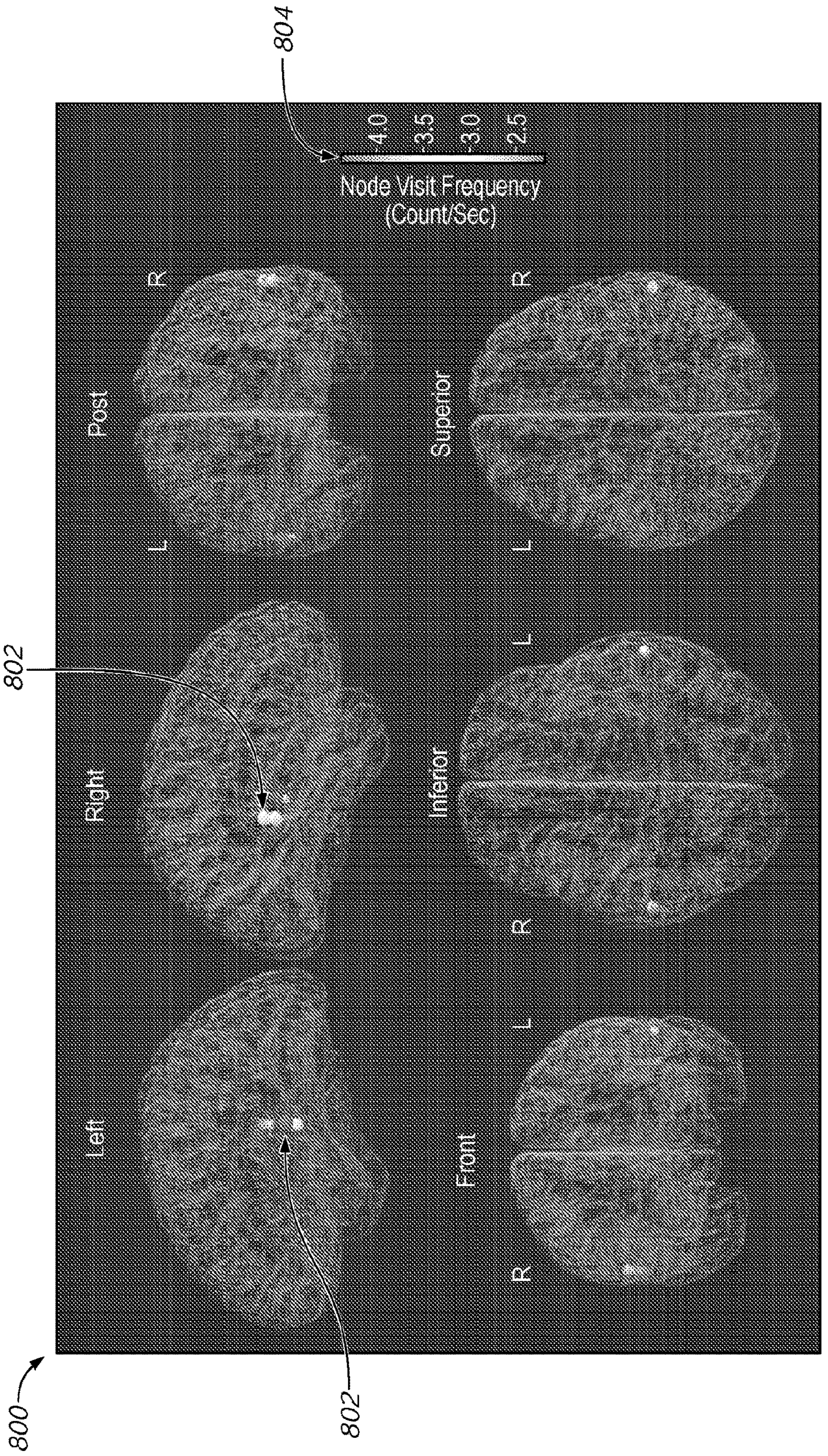
FIG. 8 example node visit frequency result of a seizure according to examples of a disclosure.

FIG. 8 example node visit frequency result of a seizure according to examples of a disclosure. The seizure used to generate the example result 800 is the same seizure used to generate the example result 600. The result 800 is shown in left, right, posterior, anterior, inferior and superior view of the same brain. The size of a node 802 is quadratically proportional to its value (e.g., counts/sec) and a shade of the node 802 corresponds to its value as indicated by the legend 804. However, other visualization techniques for conveying the value of the node visit frequency may be used in other examples. For example, text indicating the value may be provided inside or next to a node.

In some examples, node transition frequency may be calculated for the 4D source localization. The node transition frequency may indicate the order in which nodes are active, particularly those nodes which are frequently active. The sequence in which nodes are active may provide information on how different brain regions interact and/or are connected. It may also provide insight on potential therapy targets, for example, interrupting communications between two regions to inhibit or reduce the severity of seizures and/or other undesirable neurological events. The node transition frequency may be calculated for source localization nodes, such as local maximums, across an analysis time window.

A node transition is when a characteristic changes from one node to another node between time points. For example, when a local maximum node at one time point is different than a local maximum node at a different time point, the activity associated with the local maximum is said to "transition" from one node to the other. A node transition connection is a transition from one node (e.g., one local maximum node) a first time to another node (e.g., another local maximum node) at a second time. The connection will be illustrated by an arrow starting at the node of the first time and ending at the node of the second time. If there are multiple nodes (e.g., multiple local maximums) at one or more times, the two nodes with a shortest Euclidean distance will be connected. For example, Node A and Node B are local maximums at Time 0 and Node C and Node D are local maximums at Time 1. If Node A is closer (based on the Euclidean distance) to Node C than Node D, and Node A is closer to Node C than Node B, an arrow will be drawn between Node A and Node C. If a same node is present at both times (e.g., is a multiple local maximum at both times), no arrow will be drawn between the node and another node.

In addition to providing arrows indicating the transitions, numerical results for node transition frequency may be provided. After all the time points of the analysis time window have been analyzed, a number of times that a transition from one node to another occurred within the analysis time window is counted. The result may be a number of counts (e.g., transitions). In some examples, the number of times may be divided by the duration of the analysis time window, and the result may be a number of counts divided by time (counts/sec).

Figure 9:
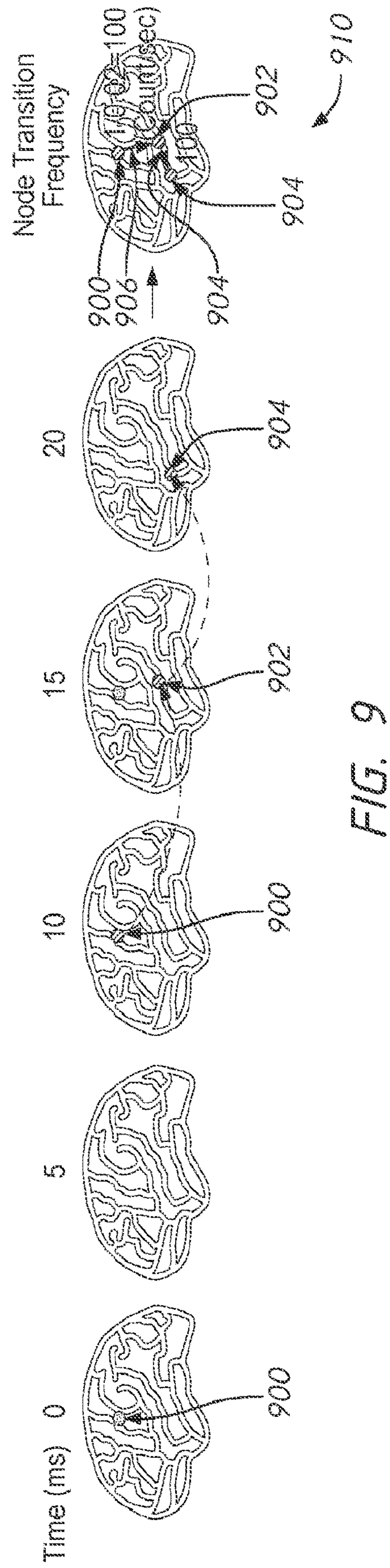
FIG. 9 graphically illustrates an example computation of a node transition frequency for three nodes according to examples of the disclosure.

FIG. 9 graphically illustrates an example computation of a node transition frequency for three nodes according to examples of the disclosure. Although the example shown in FIG. 9 includes three nodes, other numbers of nodes may be used in other examples (e.g., 2, 4, 5, etc.). A first node 900 is labeled as a local maximum at time 0 ms and 10 ms. A second node 902, corresponding to a different region of the brain than node 900, is labeled as a local maximum at time 15 ms. A third node 904, corresponding to a different region of the brain than nodes 900 and 902, is labeled as a local maximum at time 20 ms. Both a graphical and a numerical result may be provided for the node transition frequency. As shown in image 910, arrow 906 indicates the transition of the local maximum from node 900 to node 902 between times 10 ms and 15 ms, and arrow 908 indicates the transition of the local maximum from node 902 to 904 between times 15 ms and 20 ms. The direction of the arrow indicates the temporal order of the transition. For example, the initial local maximum was node 900 and at a later time, the local maximum was node 902. Thus the origin of the arrow is at node 900 and the tip of the arrow is at node 902.

Additionally, the number of transitions between nodes 900 and 902 is counted (1) and divided by the analysis time window (0.02 sec) to provide a numerical value of the node transition frequency (100 counts/sec). The numerical value is also provided for the node transition frequency between nodes 902 and 904, which in this example, happens to be the same as the node transition frequency of nodes 900 and 902 (100 counts/sec). However, the node transition frequencies between different nodes may be different in other examples.

Figure 10:
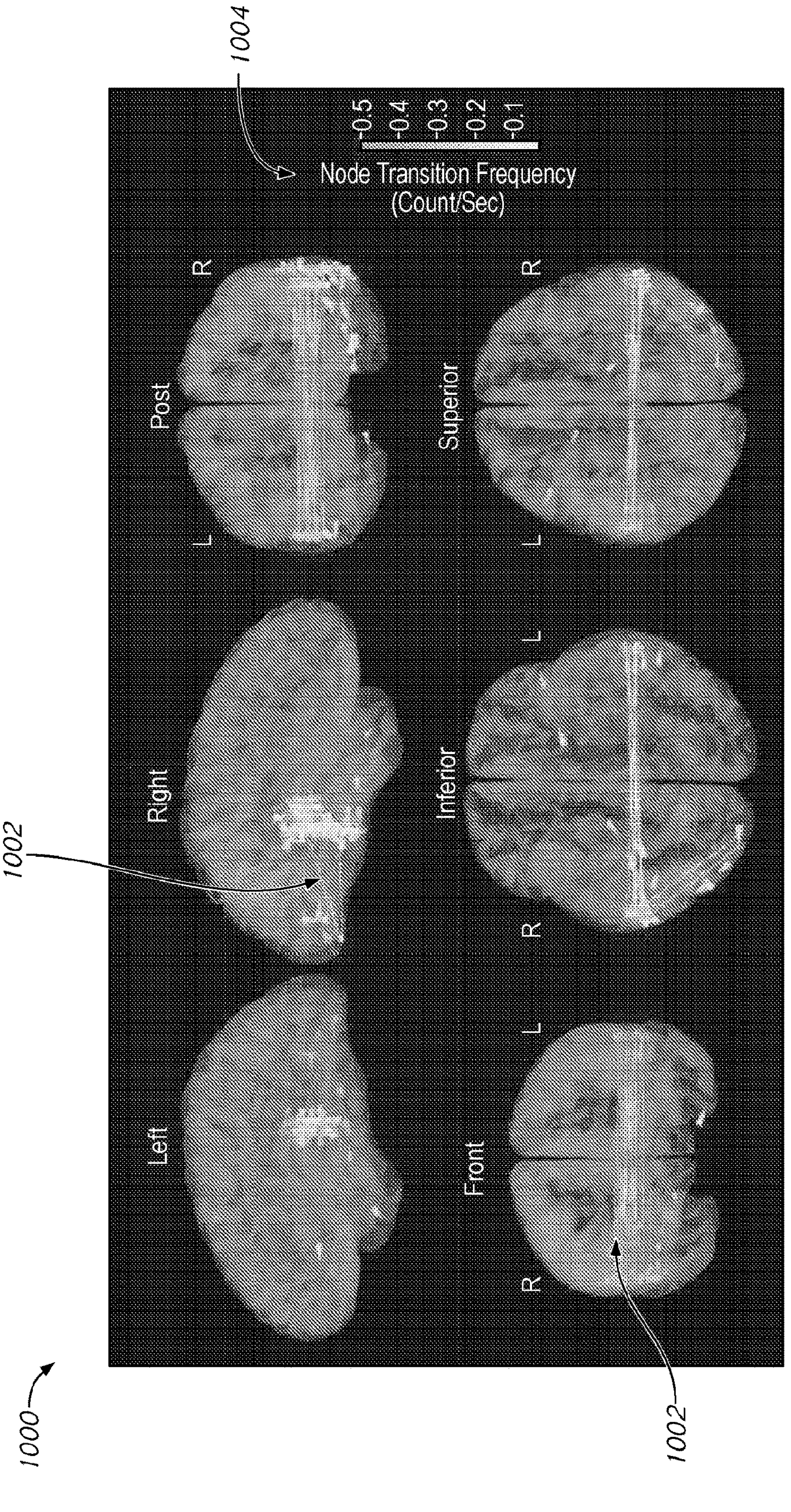
FIG. 10 example node transition frequency result of a seizure according to examples of a disclosure.

FIG. 10 example node transition frequency result of a seizure according to examples of a disclosure. The seizure used to generate the example result 1000 is the same seizure used to generate the example result 600. The result 1000 is shown in left, right, posterior, anterior, inferior and superior view of the same brain. The arrows 1002 indicate the nodes involved in one or more transitions, and the direction of the arrows indicate the temporal order of the node transitions. In the example shown in FIG. 10, a shade of the arrow indicates a numerical value of the node transition frequency as indicated by the legend 1004. However, other visualization techniques for conveying the value of the node transition frequency may be used in other examples. For example, the frequency may be provided as text over the arrow.

In some examples, a node transition polarity may be calculated for the 4D source localization. The node transition polarity may be based, at least in part, on the node transition frequency. The node transition polarity may provide information on the average inward/outward polarity of brain regions during activity transition. That is, the node transition polarity may indicate whether a region of the brain is more often a "receiver" of inputs from other regions of the brain or a "transmitter" of outputs to other regions of the brain. In some cases, if the region of the brain is a transmitter, it may trigger activity in other regions of the brain and if the region of the brain is a receiver, it may exhibit activity responsive to inputs from other brain regions. It may also provide insight on potential therapy targets, for example, preventing a brain region from transmitting and/or receiving signals to inhibit or reduce the severity of seizures and/or other undesirable neurological events.

For each node that was connected to another node by an arrow during calculation of the node transition frequency calculations, such as those described with reference to FIGS. 9 and 10, a number of times the arrows pointed to the node (e.g., activity transitioned from another node to the node) may be counted and a number of times the arrows pointed from the node (e.g., activity transitioned from the node to another node) may be counted. A positive or negative value may be assigned to the directions of the arrows. For example, arrows pointing to the node may be positive and arrows pointing from the node may be negative. The total number of arrows (e.g., connections) may be summed. If the sum of all the connections of the node is positive (e.g., more arrows pointed to the node), the polarity of the node may be inward. If the sum of all the connections of the node is negative (e.g., more arrows pointed from the node), the polarity of the node may be outward.

Figure 11A:
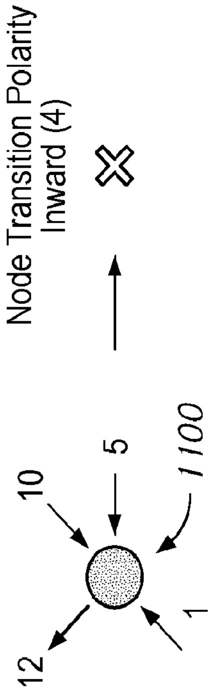
FIGS. 11A and B graphically illustrate example computations of node transition polarity for two node according to examples of the disclosure.
Figure 11B:
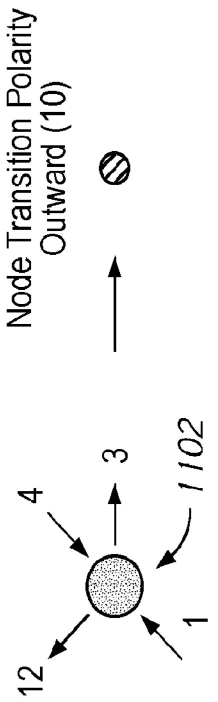

FIG. 11 graphically illustrates example computations of node transition polarity for two nodes according to examples of the disclosure. A node 1100 was found to transition to one node (not shown) 12 times during a previous computation of node transition frequency, and transition from three nodes (not shown) 1, 5, and 10 times during the previous computation of node transition frequency. Thus, node 1100 had a total of 12 outgoing connections and 16 incoming connections. Subtracting 16 from 12 results in −4. Thus, node 1100 has an inward polarity with a magnitude of 4.

A node 1102 was found to transition to one node (not shown) 12 times and transition to another node (not shown) 3 times during a previous computation of node transition frequency, and transition from two nodes (not shown) 1 and 4 times during the previous computation of node transition frequency. Thus, node 1102 had a total of 15 outgoing connections and 5 incoming connections. Subtracting 5 from 15 results in 10. Thus, node 1102 has an outward polarity with a magnitude of 10.

Figure 12:
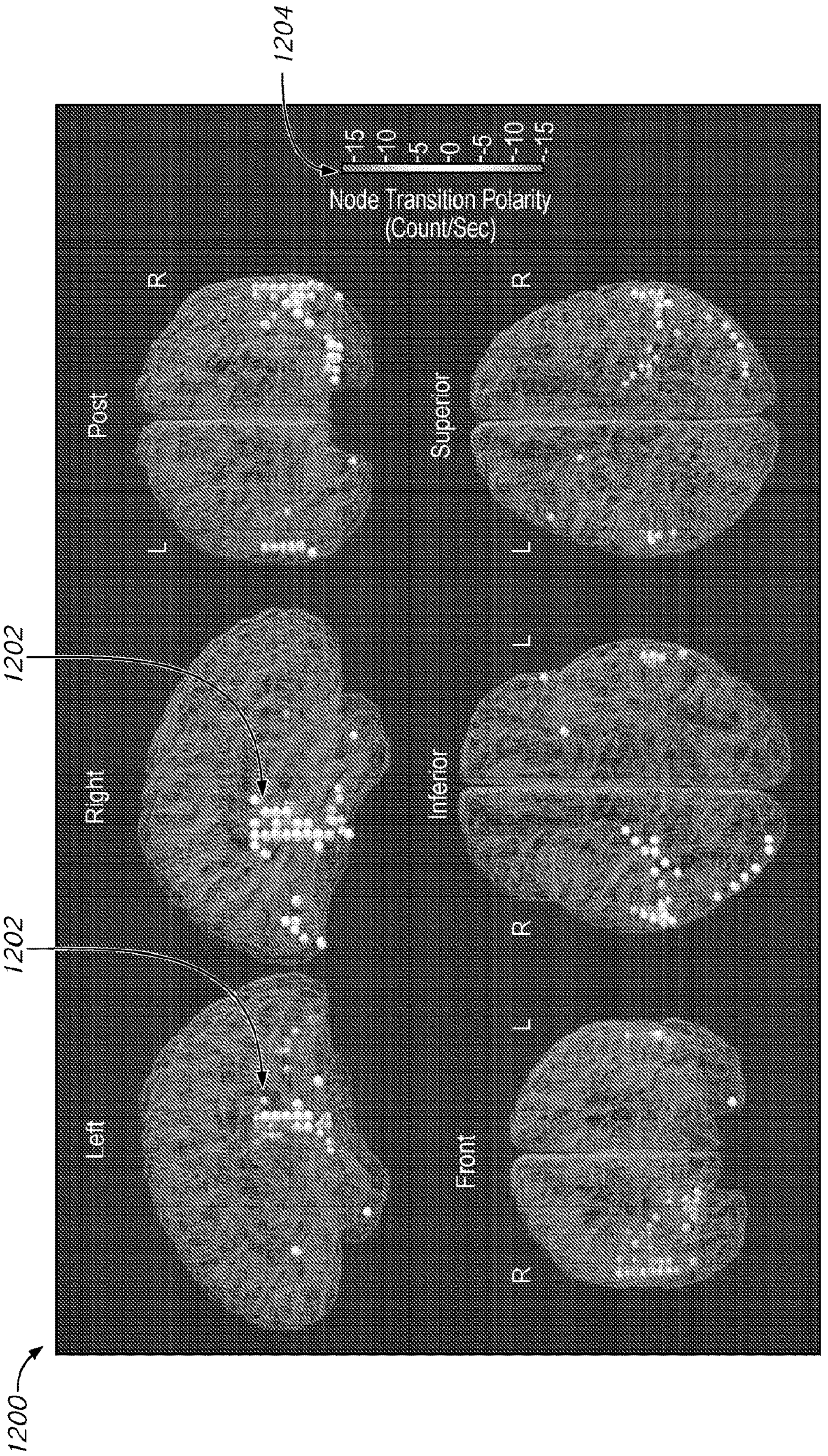
FIG. 12 example node transition polarity result of a seizure according to examples of a disclosure.

FIG. 12 example node transition polarity result of a seizure according to examples of a disclosure. The seizure used to generate the example result 1200 is the same seizure used to generate the example result 600. The result 1200 is shown in left, right, posterior, anterior, inferior and superior view of the same brain. In the example shown in FIG. 12, a shade of the node indicates the polarity and magnitude thereof according to the legend 1204. However, other visualization techniques for conveying the value of the node transition polarity may be used in other examples. For example, different colors may be used for different polarities and/or magnitudes. In another example, different shapes may be used for different polarities (e.g., “x“for inward polarity and”.” for outward polarity).

Various metrics, such as maximum amplitude projection, node visit frequency, node transition frequency, and/or node transition polarity, may be computed from the 4D source localization, and the results may be provided numerically and/or as an image as described with reference to FIGS. 5-12. The data from the metrics and the visualization thereof may be provided via a user interface. In some examples the data and visualization of the metrics may be displayed concurrently with other data, such as 2D EEG plots (e.g., plot 100), contour maps (e.g., contour map 104), 3D source localization (e.g., 3D source localization 110, 4D source localization (e.g., source localizations 200, 202), or combinations thereof on the user interface. The user interface may be included with and/or communicate with a computing device. For example, the user interface may be provided on a screen or touchscreen of a computing device.

Figure 13:
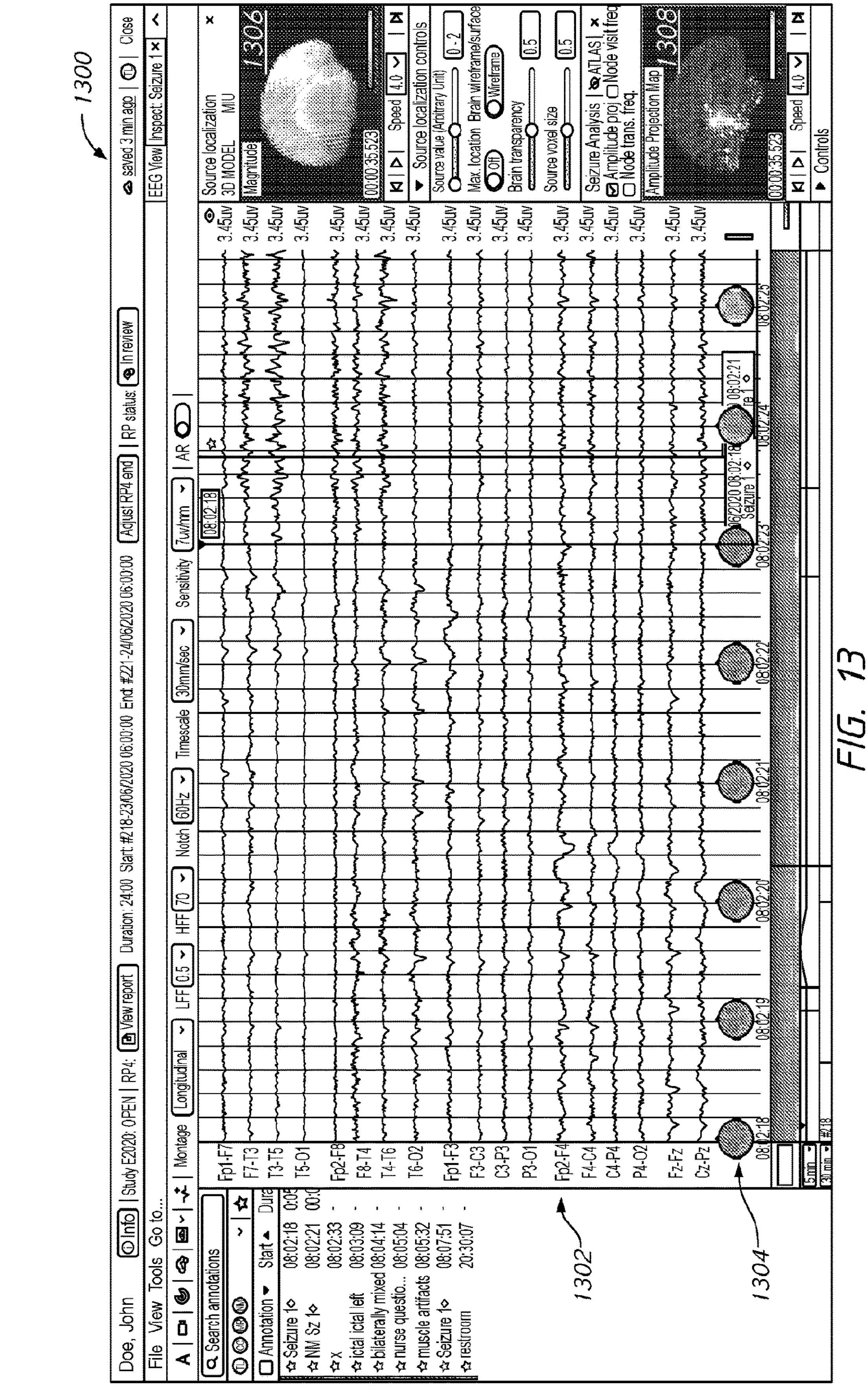
FIG. 13 is an example user interface displaying source localization data shown together with EEG data according to examples of the disclosure.

FIG. 13 is an example user interface displaying source localization data shown together with EEG data according to examples of the disclosure. The user interface 1300 provides plots of the EEG traces over time 1302 as well as a graphical depiction 1304 of a subject’s scalp with a color gradient overlaid indicating the maximum and/or standard deviation of electrical signals over different periods of times (e.g. every 1 second) on the scalp. This graphical depiction 1304 is similar to contour map 104 in FIG. 1. In box 1306, a 3D rendering of a model brain is shown overlaid with a 3D source localization with a color gradient to indicate source localization estimates of brain electrical activities on a surface of the brain in addition to various user controls. This is similar to the 3D source localization 110 in FIGS. 1 and 200 and 202 in FIG. 2. The color gradient may vary for different time points as the electrical activity in the brain changes. Thus, the 3D rendering in some cases may not be a static image, but a series of images over time (e.g., sequence, movie) to provide a 4D source localization. The user controls allow the user to control various display functions such as speed of the movie, threshold of the displayed source values, brain transparency, display voxel size, etc. Below box 1306, a visualization of the maximum amplitude projection 1308 is provided. The maximum amplitude projection 1308 includes an additional 3D rendering of a model brain is shown overlaid with circles representing nodes, where the nodes are color coded to qualitatively indicate values calculated for maximum amplitude projection for the various nodes. Similar to the source localization estimates, the nodes and/or color coding thereof may change for different time durations (e.g. every 1 second, the whole seizure, or during a time range of interest that user selected) and may also be provided as a movie. The maximum amplitude projection 1308 may have been generated as described with reference to FIGS. 5 and 6 in some examples.

A user may choose some or all of the data provided by providing inputs via the user interface.

Figure 14:
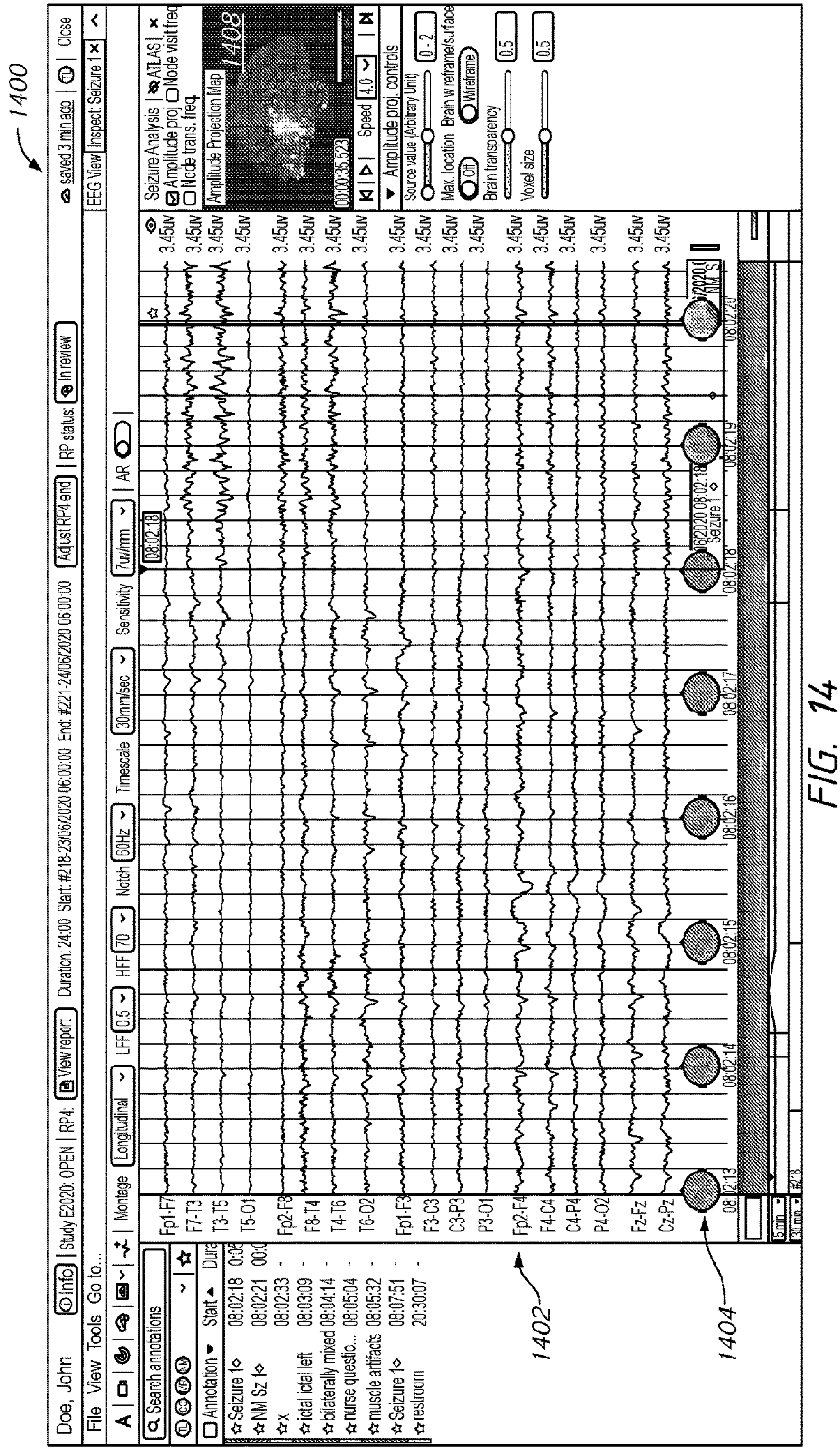
FIG. 14 is an example user interface displaying maximum amplitude projection shown together with EEG data according to examples of the disclosure.

FIG. 14 is an example user interface displaying maximum amplitude projection shown together with EEG data according to examples of the disclosure. The user interface 1400 provides plots of the EEG traces 1402 over time as well as a graphical depiction 1404 of a subject’s scalp with a color gradient overlaid indicating the maximum and/or standard deviation of electrical signals over different period of times on the scalp, similar to FIG. 13. As indicated by box 1408, a 3D rendering of a model brain is shown overlaid with circles representing nodes, where the nodes are color coded to qualitatively indicate values calculated for maximum amplitude projection for the various nodes. The nodes and/or color coding thereof may change for different time points, thus, the 3D rendering may be a series of images over time viewing frame-by-frame and/or as a movie. The user controls allow the user to control various display functions such as speed of the movie, threshold of the displayed maximum amplitude value, brain transparency, voxel size, etc.

Figure 15:
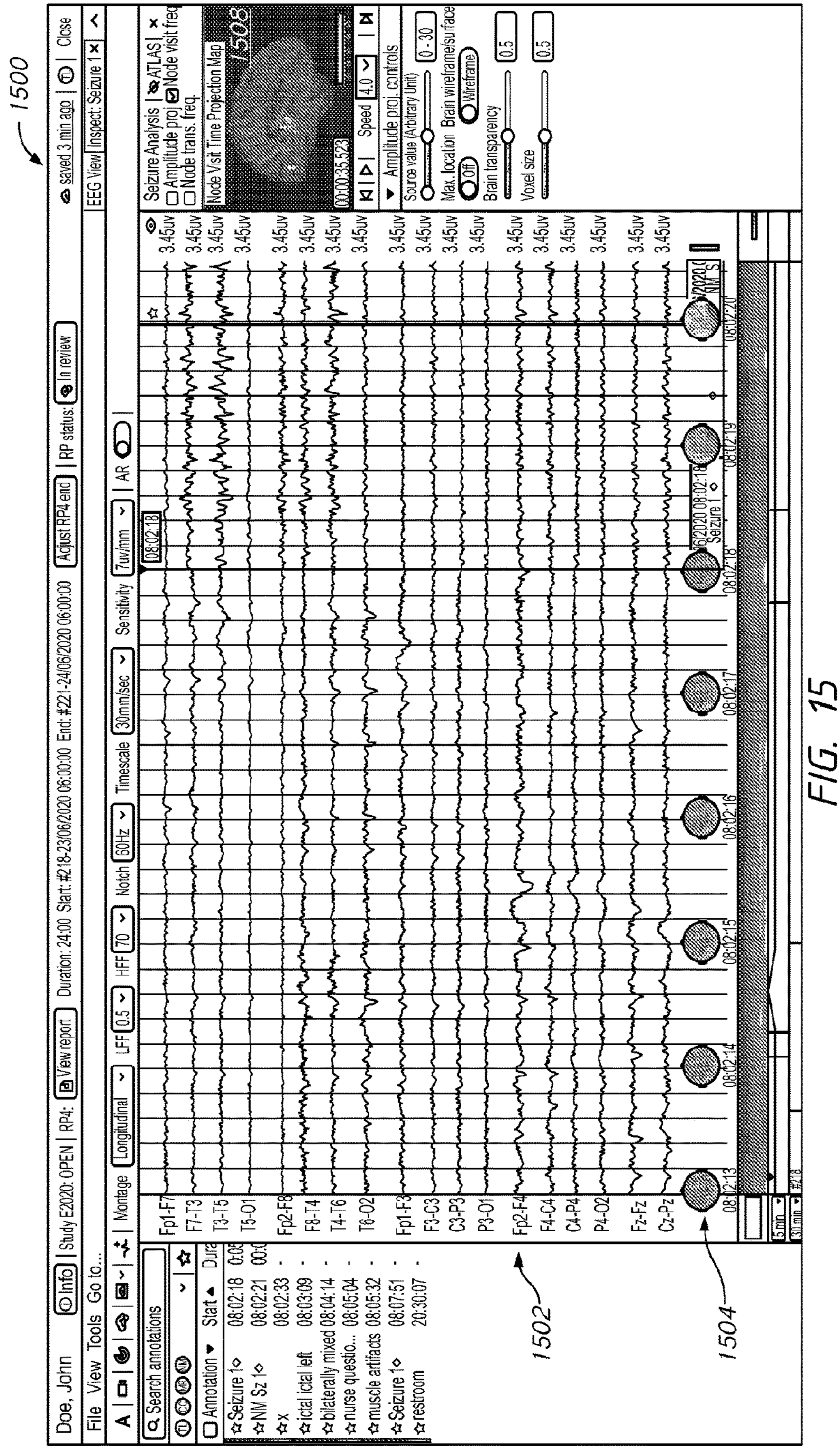
FIG. 15 is an example user interface displaying node visit frequency shown together with EEG data according to examples of the disclosure.

FIG. 15 is an example user interface displaying node visit frequency shown together with EEG data according to examples of the disclosure. The user interface 1500 provides plots of the EEG traces 1502 over time as well as a graphical depiction 1504 of a subject’s scalp with a color gradient overlaid indicating the maximum and/or standard deviation of electrical signals over different period of times on the scalp, similar to FIG. 13 and FIG. 14. As indicated by box 1508, a 3D rendering of a model brain is shown overlaid with circles representing nodes, where the nodes are color coded to qualitatively indicate values calculated for node visit frequency for the various nodes. The nodes and/or color coding thereof may change for different time points, thus, the 3D rendering may be a series of images over time that may be provided for viewing frame-by-frame and/or as a movie. The node visit frequency may have been computed as described with reference to FIGS. 7 and 8 in some examples. The user controls allow the user to control various display functions such as speed of the movie, threshold of the displayed node visit frequency (counts/second), brain transparency, voxel size, etc.

Figure 16:
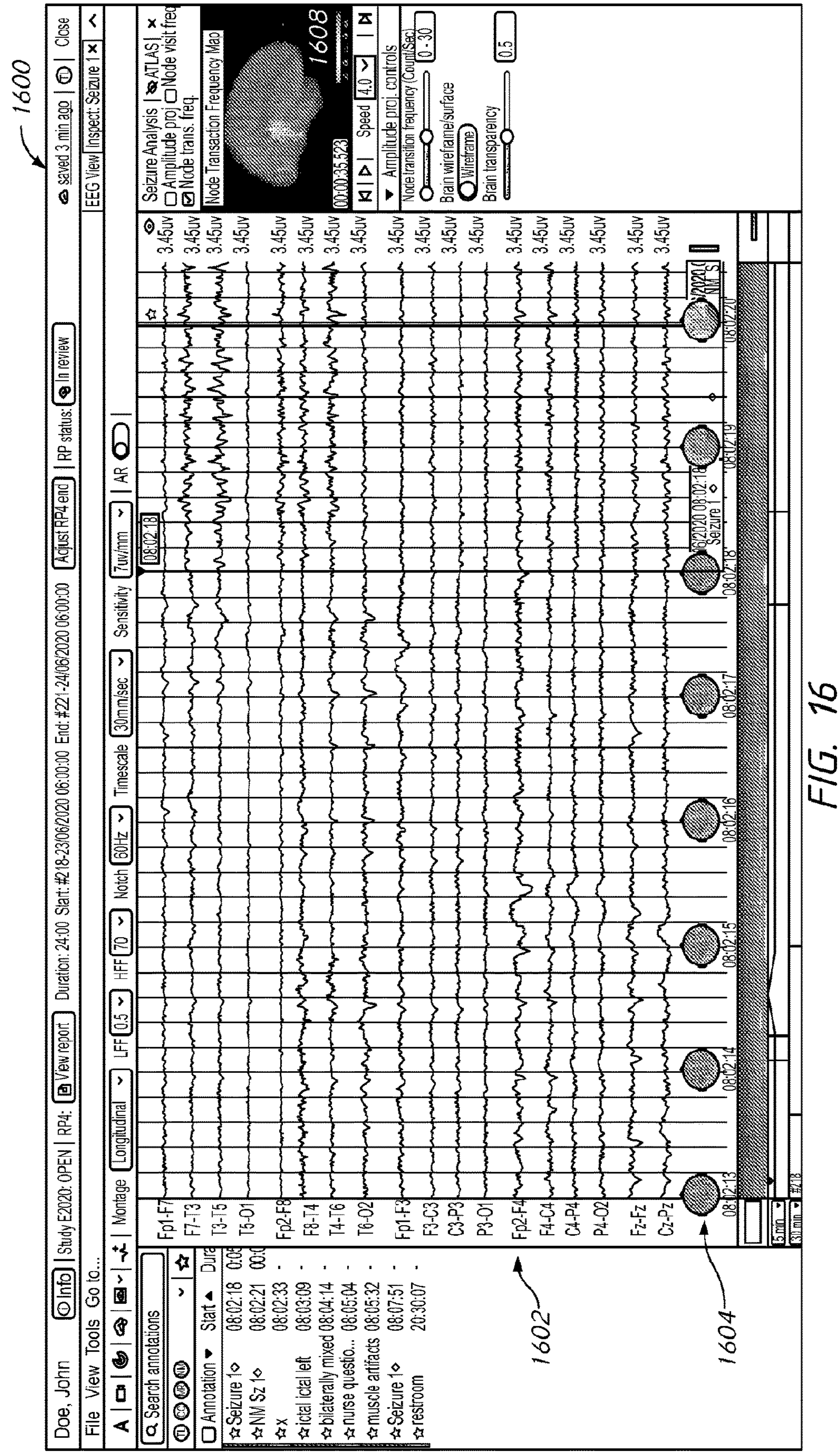
FIG. 16 is an example user interface displaying node transition frequency shown together with EEG data according to examples of the disclosure.

FIG. 16 is an example user interface displaying node transition frequency shown together with EEG data according to examples of the disclosure. The user interface 1600 provides plots of the EEG traces 1602 over time as well as a graphical depiction 1604 of a subject’s scalp with a color gradient overlaid indicating average/maximum electrical signals over different period of times on the scalp, similar to FIGS. 13-15. As indicated by box 1608, a 3D rendering of a model brain is shown overlaid with vectors, where the vectors are color coded to qualitatively indicate values calculated for node transition frequency for the various nodes (e.g., pairs of nodes). The vectors and/or color coding thereof may change for different time points, thus, the 3D rendering may be a series of images over time that may be provided for viewing frame-by-frame and/or as a movie. The node transition frequency may have been calculated as described with reference to FIGS. 9 and 10 in some examples. The user controls allow the user to control various display functions such as speed of the movie, threshold of the node visit polarity (counts/second), brain transparency, voxel size, etc.

Although FIGS. 13-16 show only one graphical representation of the calculated parameters (e.g., metrics), in other examples, the user interfaces may permit the user to visualize multiple parameters concurrently (e.g., graphical representations of both maximum amplitude projection and node visit frequency may be provided on the user interface). Furthermore, in some examples, the user interface may provide a report that summarizes the parameters calculated.

Figure 17:
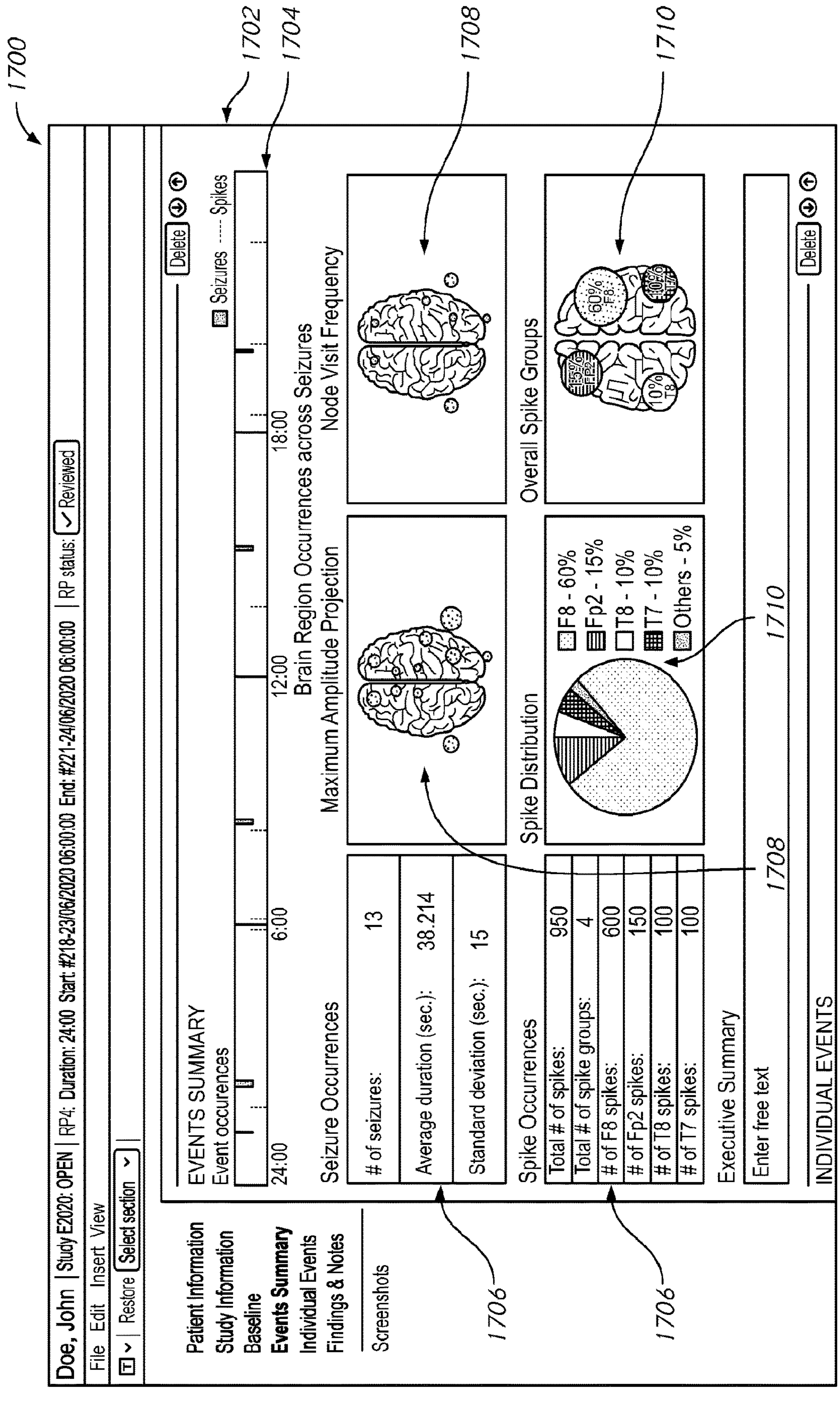
FIG. 17 is an example user interface displaying seizure analysis summary in a report according to examples of the disclosure.

FIG. 17 is an example user interface displaying seizure analysis summary in a report according to examples of the disclosure. The user interface 1700 provides a summary of one or more parameters calculated from the EEG traces as a report 1702. The report 1702 may include a timeline 1704 of epileptiform activity, various numerical statistics 1706 (e.g., number of seizures, average duration, number of spikes, etc.), one or more graphical representations of metrics (e.g., maximum amplitude projection, node visit frequency, spike groups) overlaid on images of the brain 1708, one or more charts 1710 of other parameters (e.g., spike distribution), and/or combinations thereof. In some examples, a user may be able to select the contents of the report 1702. For example, the user may provide input via one or more input devices to indicate which contents to include in the report 1702.

In some examples, the EEG data may be received and analyzed by a computing system. The computing system may calculate various metrics and may provide various outputs, such as the calculated metrics, on a display communicatively coupled to the computing system.

Figure 18:
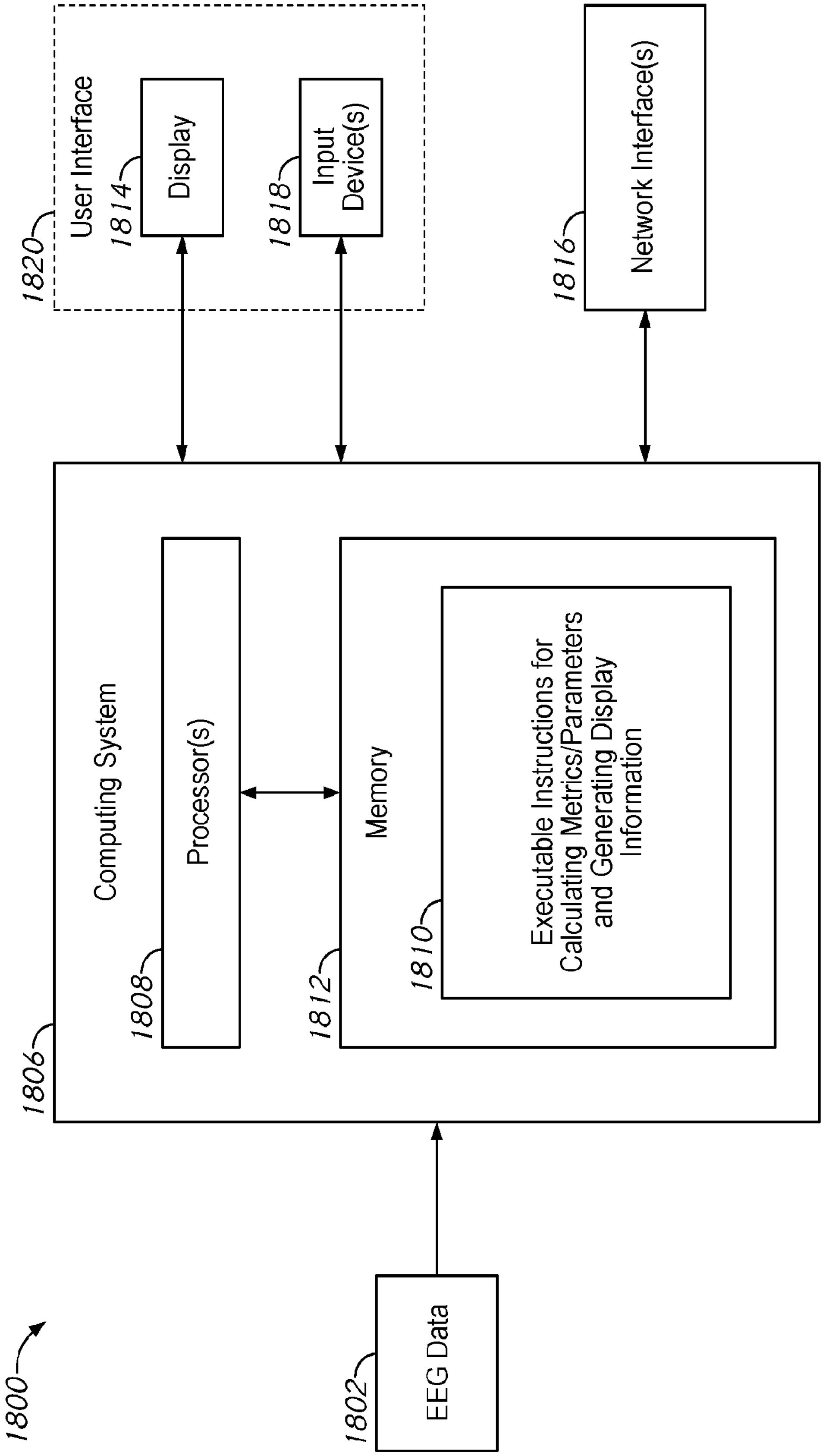
FIG. 18 is a schematic illustration of a system arranged according to examples of the disclosure.

FIG. 18 is a schematic illustration of a system arranged according to examples of the disclosure. The system 1800 includes computing system 1806, processor(s) 1808, executable instructions for calculating metrics/parameters and generating display information 1810, memory 1812, display 1814, and network interface(s) 1816. The system 1800 may receive EEG data 1802 (e.g., EEG as shown in plot 100). Additional, fewer, and/or other components may be included in system 1800 in other examples. For example, in some examples, system 1800 may include an EEG system for acquiring EEG data 1802. In other embodiments, the EEG data 1802 may further or alternatively include one or more other types of neurological activity data, such as fMRI data, The computing system 1806 may analyze the EEG data 1802 to calculate one or more metrics and/or generate display information for providing the metrics on display 1814, for example as described with reference to FIGS. 3-17. In some examples, the memory 1812 may be encoded with executable instructions 1810 for calculating the metrics and/or generating display information for the metrics. In some examples, the memory 1812 may further be encoded with executable instructions 1810 for providing a graphical user interface (GUI) that may provide text, graphics, and/or other visual information on display 1814.

The computing system 1806 may include one or more processor(s) 1808. The processor(s) 1808 may be implemented, for example, using one or more central processing units (CPUs), graphical processing units (GPUs), application-specific integrated circuits (ASICs), field programmable gate arrays (FPGA), or other processor circuitry. In some examples, the processor(s) 1808 may execute some or all of the executable instructions 1810. The processor(s) 1808 may be in communication with memory 1812. The memory 1812 may generally be implemented by any non-transitory, computer readable media (e.g., read-only memory (ROM), random access memory (RAM), flash, solid state drive, etc.). While a single memory 1812 is shown, any number may be used, and they may be integrated with the processor(s) 1808 in a single computing system 1806 and/or located within another computing system and in communication with processor(s) 1808. For example, the EEG data 1802 may be included in one computer readable medium of memory 1812 and the executable instructions 1810 may be included in another computer readable medium of memory 1812. Some or all of the media included with memory 1812 may be accessible to processor(s) 1808.

In some examples, the system 1800 may include display 1814, which may be in communication with computing system 1806 (e.g., using a wired and/or wireless connection), or the display 1814 may be integrated with the computing system 1806. The display 1814 may display one or more metrics/parameters calculated by the computing system, one or more graphics based on the metrics/parameters, EEG data 1802, and/or one or more GUI elements. For example, images, data, and/or displays such as those shown in FIGS. 1-4, 6, 8, 10, and/or 12-17 may be provided on display 1814. Any number or variety of displays may be present, including one or more LED, LCD, plasma, or other display devices.

In some examples, the system 1800 may include network interface(s) 1816. The network interface(s) 1816 may provide a communication interface to any network (e.g., LAN, WAN, Internet). The network interface(s) 1816 may be implemented using a wired and/or wireless interface (e.g., Wi-Fi, BlueTooth, HDMI, USB, etc.). The network interface(s) 1816 may communicate data which may include EEG data 1802 and/or metrics calculated by the computing system 1806.

In some examples, system 1800 may include various input device(s) 1818 which may be configured to receive inputs from a user. Examples of input devices include, but are not limited to, mouse, keyboard, trackball, joystick, touchpad, and touchscreen. In some examples, the display 1814 may be an input device (e.g., when display 1814 is a touch screen). In some examples, input device(s) 1818 and/or display 1814 may be included in a user interface 1820, which may be, at least in part, a graphical user interface. In some examples, the user may be able to provide an input via one or more of the input device(s) 1818 to actions performed by the computing system 1806. For example, a user may provide inputs to determine which metrics are calculated and/or what metrics are provided on display 1814.

Figure 19:
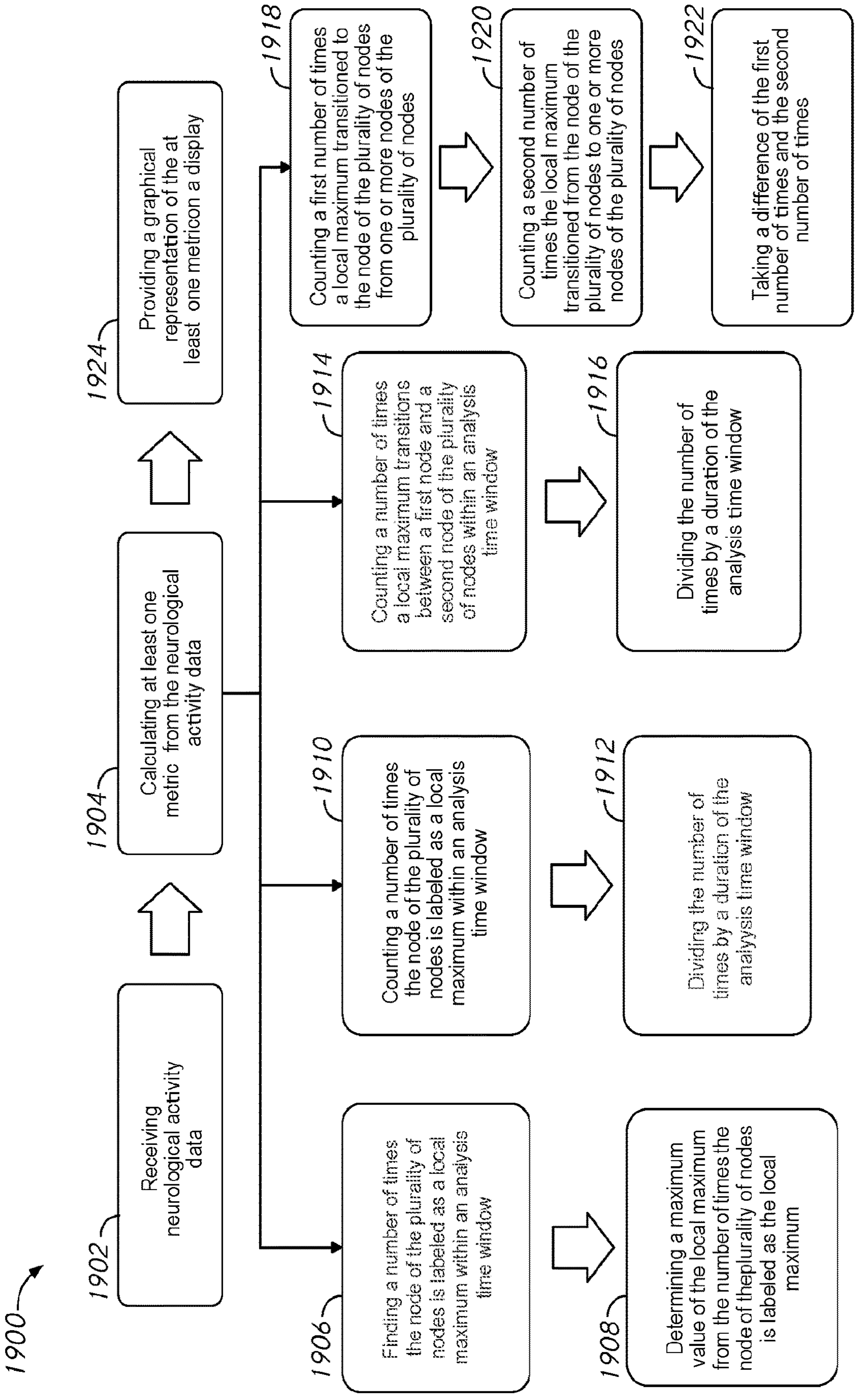
FIG. 19 is a flow chart of a method according to examples of the present disclosure.

FIG. 19 is a flow chart of a method according to examples of the present disclosure. In some examples, the method shown in flow chart 1900 may be performed in whole or in part by a computing system, such as computing system 1800.

At block 1902 "receiving neurological activity data" may be performed. In some examples, the neurological activity data may be EEG data received from an EEG device. In other embodiments, the neurological activity data may be fMRI data received from an MRI system. Other data types may be received from other devices in other examples. In some embodiments, the neurological activity data may include a three dimensional (3D) source localization including a plurality of nodes, wherein individual ones of the plurality of nodes corresponds to a portion of a brain.

At block 1904, "calculating at least one metric from the neurological activity data" may be performed. In some examples, the at least one metric may include a maximum amplitude projection, a node visit frequency, a node transition frequency, a node transition polarity, or a combination thereof.

As indicated by blocks 1906 and 1908, calculating the maximum amplitude projection of a node of the plurality nodes may include "finding a number of times the node of the plurality of nodes is labeled as a local maximum within an analysis time window" and "determining a maximum value of the local maximum from the number of times the node of the plurality of nodes is labeled as the local maximum."

As indicated by blocks 1910 and 1912, calculating the node visit frequency for a node of the plurality of nodes may include "counting a number of times the node of the plurality of nodes is labeled as a local maximum within an analysis time window" and "dividing the number of times by a duration of the analysis time window."

As indicated by blocks 1914 and 1916, calculating the node transition frequency may include "counting a number of times a local maximum transitions between a first node and a second node of the plurality of nodes within an analysis time window" and "dividing the number of times by a duration of the analysis time window."

As indicated by blocks 1918, 1920, and 1922 calculating the node transition polarity for a node of the plurality of nodes may include "counting a first number of times a local maximum transitioned to the node of the plurality of nodes from one or more nodes of the plurality of nodes," "counting a second number of times the local maximum transitioned from the node of the plurality of nodes to one or more nodes of the plurality of nodes" and "taking a difference of the first number of times and the second number of times." In some examples, the node of the plurality of nodes has an inward polarity when the first number of times is greater than the second number of times and the node of the plurality of nodes has an outward polarity when the second number of times is greater than the first number of times.

At block 1924 "providing a graphical representation of the at least one metric on a display" may be performed. For example, the graphical representation may include a graphical representation of the metrics such as those shown in FIGS. 6, 8, 10, and/or 12-17.

In some examples, the method shown in flow chart 1900 may further include preprocessing the neurological activity, which may include comparing values of the neurological activity data to a threshold value, based on the comparing, discarding or ignoring one or more of the values of the neurological activity data, and from remaining values of the neurological activity data, calculating at least one local maximum.

One or more metrics may be calculated as disclosed herein to summarize 4D source localizations, such as 4D seizure source localizations. In some applications, this may reduce the time necessary to generate and/or interpret 4D source localization. Metrics such as maximum amplitude projection, node visit frequency, node transition frequency, and/or node transition polarity may be calculated as disclosed herein. These metrics may then be provided in various formats, such as through text, charts, generated images, or a combination thereof. The metrics may be used to diagnose, to determine and/or adjust treatment, and/or to take other actions.

From the foregoing it will be appreciated that, although specific embodiments have been described herein for purposes of illustration, various modifications may be made while remaining with the scope of the claimed technology.

What is claimed is:

1. A system comprising:

at least one processor;

a memory accessible to the at least one processor, the memory encoded with computer-readable instructions that when executed, cause the system to calculate at least one metric comprising a maximum amplitude projection, a node visit frequency, a node transition frequency, a node transition polarity, or a combination thereof, from neurological activity data; and a display communicatively coupled to the at least one processor, wherein the computer-readable instructions when executed, further cause the system to provide a graphical representation of the at least one metric on the display, wherein the graphical representation of the at least one metric comprises a node of a three dimensional (3D) source localization overlaid on an image of a brain and a second node of the 3D source localization and an arrow between the node and the second node, wherein a direction of the arrow indicates a transition of a local maximum between the node and the second node.

2. The system of claim 1, wherein the neurological activity data comprises electroencephalography data.

3. The system of claim 1, wherein the computer-readable instructions when executed, further cause the system to provide a report on the display, wherein the report comprises a plurality of contents comprising one or more graphical representations of the at least one metric and further comprises a timeline of the neurological activity data, one or more statistics, one or more additional parameters, or a combination thereof.

4. The system of claim 3, further comprising an input device configured to receive a user input, wherein the user input indicates which ones of the plurality of contents are included in the report.

5. A method comprising:

receiving neurological activity data;

calculating at least one metric comprising a maximum amplitude projection, a node visit frequency, a node transition frequency, a node transition polarity, or a combination thereof, from the neurological activity data of at two nodes of a plurality of nodes of a three dimensional source localization of the neurological activity data; and providing a graphical representation of the at least one metric on a display wherein the graphical representation of the at least one metric comprises a first node of the plurality of nodes overlaid on an image of a brain, a second node of the plurality of nodes, and an arrow between the first node and the second node, wherein a direction of the arrow indicates a transition of a local maximum between the first node and the second node.

6. The method of claim 5, wherein individual ones of the plurality of nodes correspond to a portion of the brain.

7. The method of claim 6, wherein calculating the maximum amplitude projection of a node of the plurality of nodes comprises:

finding a number of times the node of the plurality of nodes is labeled as a local maximum within an analysis time window; and determining a maximum value of the local maximum from the number of times the node of the plurality of nodes is labeled as the local maximum within the analysis time window.

8. The method of claim 6, wherein calculating the node visit frequency for a node of the plurality of nodes comprises:

counting a number of times the node of the plurality of nodes is labeled as a local maximum within an analysis time window; and dividing the number of times by a duration of the analysis time window.

9. The method of claim 6, wherein calculating the node transition frequency comprises:

counting a number of times a local maximum transitions between the first node and the second node of the plurality of nodes within an analysis time window; and dividing the number of times by a duration of the analysis time window.

10. The method of claim 6, wherein calculating the node transition polarity for a node of the plurality of nodes comprises:

counting a first number of times a local maximum transitioned to the node of the plurality of nodes from one or more nodes of the plurality of nodes;

counting a second number of times the local maximum transitioned from the node of the plurality of nodes to one or more nodes of the plurality of nodes; and taking a difference of the first number of times and the second number of times, wherein the node of the plurality of nodes has an inward polarity when the first number of times is greater than the second number of times and the node of the plurality of nodes has an outward polarity when the second number of times is greater than the first number of times.

11. The method of claim 5, further comprising preprocessing the neurological activity data by:

comparing values of the neurological activity data to a threshold value;

based on the comparing, discarding or ignoring one or more of the values of the neurological activity data; and from remaining values of the neurological activity data, calculating at least one local maximum.

12. The method of claim 5, wherein a size of a node of the plurality of nodes is proportional to a value of the maximum amplitude projection or a value of the node visit frequency for the node.

13. The method of claim 5, wherein a shade, a color, or a combination thereof of a node of the plurality of nodes, is indicative of a value for the maximum amplitude projection, the node visit frequency, or the node transition polarity for the node.

14. The method of claim 5, wherein a shade, a color, or a combination thereof of the arrow indicates a frequency of the transition over an analysis time window.

15. The method of claim 5, further comprising providing a report on the display, wherein the report comprises a plurality of contents comprising one or more graphical representations of the at least one metric and further comprises a timeline of the neurological activity data, one or more statistics, one or more additional parameters, or a combination thereof.

* * * * *